(12) United States Patent
Allison

(10) Patent No.: US 7,407,475 B2
(45) Date of Patent: *Aug. 5, 2008

(54) MODIFIED ANNEXIN PROTEINS, AND METHODS AND COMPOSITIONS FOR USING THEM

(75) Inventor: Anthony Allison, Belmont, CA (US)

(73) Assignee: Alavita Pharmaceuticals, Inc., Mountainview, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/110,306

(22) Filed: Apr. 20, 2005

(65) Prior Publication Data

US 2005/0197295 A1   Sep. 8, 2005

Related U.S. Application Data

(63) Continuation of application No. 10/080,370, filed on Feb. 21, 2002, now Pat. No. 6,962,903.

(60) Provisional application No. 60/332,582, filed on Nov. 21, 2001, provisional application No. 60/270,402, filed on Feb. 21, 2001.

(51) Int. Cl.
*A61K 38/00* (2006.01)

(52) U.S. Cl. ............................ 500/300; 500/350

(58) Field of Classification Search ............... None
See application file for complete search history.

(56) References Cited

U.S. PATENT DOCUMENTS

| | | | |
|---|---|---|---|
| 4,002,531 A | 1/1977 | Royer et al. |
| 4,179,337 A | 12/1979 | Davis et al. |
| 4,507,229 A | 3/1985 | Bohn et al. |
| 4,732,891 A | 3/1988 | Maki et al. |
| 4,736,018 A | 4/1988 | Reutelingsperger et al. |
| 4,897,355 A | 1/1990 | Eppstein et al. |
| 4,937,324 A | 6/1990 | Fujikwa et al. |
| 4,965,251 A | 10/1990 | Stamatoyannopoulos |
| 5,066,787 A | 11/1991 | Reutelingsperger et al. |
| 5,066,788 A | 11/1991 | Reutelingsperger et al. |
| 5,097,019 A | 3/1992 | Lobermann et al. |
| 5,225,537 A | 7/1993 | Foster et al. |
| 5,229,367 A | 7/1993 | Perretti et al. |
| 5,258,497 A | 11/1993 | Reutilingsperger et al. |
| 5,290,915 A | 3/1994 | Nakao et al. |
| 5,296,467 A | 3/1994 | Reutelingsperger et al. |
| 5,360,789 A | 11/1994 | Nakao et al. |
| 5,484,711 A | 1/1996 | Wallner et al. |
| 5,589,395 A | 12/1996 | Romisch et al. |
| 5,591,633 A | 1/1997 | Saino et al. |
| 5,608,060 A | 3/1997 | Axworthy et al. |
| 5,612,460 A | 3/1997 | Zalipsky et al. |
| 5,632,986 A | 5/1997 | Tait et al. |
| 5,837,842 A | 11/1998 | Hauptmann |
| 5,849,600 A | 12/1998 | Nixon et al. |
| 5,955,437 A | 9/1999 | Reutelingsperger |
| 5,968,477 A | 10/1999 | Kasina et al. |
| 6,169,078 B1 | 1/2001 | Hughes et al. |
| 6,171,577 B1 | 1/2001 | Reno et al. |
| 6,242,570 B1 | 6/2001 | Sytkowski et al. |
| 6,312,694 B1 | 11/2001 | Thorpe et al. |
| 6,323,313 B1 | 11/2001 | Tait et al. |
| 6,358,508 B1 | 3/2002 | Ni et al. |

FOREIGN PATENT DOCUMENTS

| | | |
|---|---|---|
| DE | 19541284 A1 | 5/1996 |
| EP | 0318703 | 7/1989 |
| JP | 04198195 A * | 7/1992 |
| JP | 5001096 | 1/1993 |
| JP | 6116286 | 4/1994 |
| JP | 7072147 | 3/1995 |
| JP | 7072149 | 3/1995 |
| WO | WO91/07187 | 5/1991 |
| WO | WO91/16882 | 11/1991 |
| WO | WO92/07870 | 5/1992 |
| WO | WO 92/19279 | 11/1992 |
| WO | WO94/01554 | 1/1994 |
| WO | WO 95/34315 | 12/1995 |
| WO | WO96/03655 | 2/1996 |
| WO | WO9717084 | 5/1997 |
| WO | WO 97/24440 | 7/1997 |
| WO | WO98/01563 | 1/1998 |
| WO | WO 98/04294 | 2/1998 |
| WO | WO 98/31383 | 7/1998 |
| WO | WO99/02992 | 1/1999 |
| WO | WO99/19470 | 4/1999 |
| WO | WO 99/19470 | 4/1999 |
| WO | WO99/24054 | 5/1999 |
| WO | WO99/48916 | 9/1999 |
| WO | WO0002587 | 1/2000 |
| WO | WO98/29442 | 2/2000 |
| WO | WO00/10673 | 3/2000 |

(Continued)

OTHER PUBLICATIONS

Seffernick et al. (J. Bacteriology, vol. 183, pp. 2405-2410, 2001.*

(Continued)

*Primary Examiner*—Hope A Robinson
(74) *Attorney, Agent, or Firm*—Swanson & Bratschun, L.L.C.

(57) ABSTRACT

A modified annexin protein, preferably annexin V, is used to prevent thrombosis without increasing hemorrhage. Annexin binds to phosphatidylserine on the outer surface of cell membranes, thereby preventing binding of the prothrombinase complex necessary for thrombus formation. It does not, however, affect platelet aggregation necessary for hemostasis. The modified annexin molecule can be a homodimer of annexin, an annexin molecule coupled to one or more polyethylene glycol chains, or an annexin molecule coupled to another protein. By increasing the molecular weight of annexin, the modified annexin is made to remain in circulation for sufficient time to provide a sustained therapeutic effect.

3 Claims, 2 Drawing Sheets

FOREIGN PATENT DOCUMENTS

| | | |
|---|---|---|
| WO | WO00/11026 | 3/2000 |
| WO | WO00/12547 | 3/2000 |
| WO | WO00/38517 | 7/2000 |
| WO | WO01/11372 | 2/2001 |
| WO | WO02087498 | 11/2002 |

OTHER PUBLICATIONS

Wells, Biochemistry, vol. 29, pp. 8509-8517, 1990.*
D'Amico et al. (2000) FASEB J 14:1867-1869.
Robinson et al. (1998) PNAS USA 95:5929-5934.
Gerke et al. (2002) Physiol Rev 82:331-371.
D'Amico et al. (2000) FASEB J Article 10. 1096/99-0602FJE.
Tait, J. et al. Prourokinase-Annexin V Chimera. Journal of Biological Chemistry. Sep. 15, 1995, vol. 270, No. 27, pp. 21594-21599, especially Abstract.
Pepinsky et al. A dimeric form of lipocortin-1 in human placenta. Biochemistry Journal. 1989, vol. 263, pp. 97-103.
Rand et al. Antiphospholipid Antibodies Accelerate Plasma Coagulation by Inhibiting Annexin-V Binding to Phospholipids. A Lupus procoagulant phenomenon. Blood. Sep. 1, 1998, vol. 92, No. 5, pp. 1652-1660.
Benz and Hofmann, *Biol. Chem.* 378:177-183 (1997).
Burger, *FEBS Lett.* 329:25-28 (1993).
Campos et al., *Biochemistry* 37:8004-8008 (1998).
Fritsma, *IN Hemostasis and Thrombosis in the Clinical Laboratory* (Corriveau, D.M. and Fritsma, G.A. EDS)J.P. Lipincott Co., Philadelphia (1989), pp. 92-124, 1991.
Huber et al., *EMBO Journal* 9:3867 (1990).
Knauf et al., *J. Biol. Chem.* 266:15064-15070 (1988).
Thiagarajan and Benedict, *Circulation* 96:2339-2347 (1997).
Chap et al., Biochem Biophys Res Commun 1988, 150:972-978.
Funakoshi et al., Biochemistry 1987, 26:5572-5578.
Funakoshi et al., Biochemistry 1987, 26:8087-8092.
Grundmann et al., Behring Inst MITT 1988, 82:59-67.
Grundmann et al., Proc Natl Acad Sci USA 1988, 85:3708-3712.
Iwasaki et al., J Biochem (Tokyo) 1987, 102:1261-1273.
Kaplan et al., J Biol Chem 1988, 263:8037-8043.
Maurer-Fogy et al., Eur J Biochem 1988, 174:585-592.
Nakao et al., Chem Pharm Bull (Tokyo) 1990, 38:1957-1960.
Reutelingsperger et al., Eur J Biochem 1985, 151:625-629.
Reutelingsperger et al., Eur J Biochem 1988, 173:171-178.
Romisch et al., Biochem J 1990, 272:223-229.
Romisch et al., Thromb Res 1990, 60:355-366.
Rothhut et al., Biochem J 1989, 263:929-935.
Schlaepfer et al., Proc Natl Acad Sci USA 1987, 84:6078-6082.
Romisch et al., Thrombosis Res 1991, 61:93.
Sytkowski et al. (1998) Proc Natl Acad Sci USA 95:1184-1188.
Pepinsky et al. (1988) J Biol Chem 263(22):10799-10811.
Kassam et al. (1998) J Biol Chem 273(8):4790-4799.
Zanma et al. (1991) J Biochem 110(6):868-872.

Delgado et al. (1992) Critical Rev in Therapeutic Drug Carrier Systems 9(3/4):249-304.
Stueber et al. (1995) Peptide Research 8(2):78-85.
Database WPI, Section CH, Weed 200036, Derwent Publications LTD, London, Shanghai Inst Biochem Chinese Acad (2000) Abstract.
Allan et al., *Nature* 295:612-613 (1982).
Bangham et al., *J. Mol. Biol.* 23:238-252 (1965).
Behr et al., *Proc. Natl. Acad. Sci. USA* 86:6982-6986 (1989).
Bernard et al., *Am. Rev. Respir. Dis.* 144:1095-1101 (1991).
Brittain et al., *Blood* 81:2137-2143 (1993).
Chow et al., *J. Lab. Clin. Med.* 135:66-72 (2000).
Felgner et al., *Proc. Natl. Acad. Sci. USA* 86: 7413-7417 (1987).
Kuypers et al., *Blood* 87:1179-1187 (1996).
Lubin et al., *J. Clin. Invest.* 67:1643-1649 (1981).
Mayhew et al., *Biochim. Biophys. Acta* 775:169 (1984).
Meinkoth et al., *Anal. Biochem.* 138:267-284 (1984).
Merten et al., *Circulation* 99:2577-2582 (1999).
Murata et al., *Nature* 388:678-682 (1997).
Olson et al., *Biochim. Biophys. ACTA* 557:9 (1979).
Richardson et al., *Br. J. Haematol.* 41:95 (1979).
Setty et al., *Blood* 99:1564-1571 (2002).
Stratton et al., *Circulation* 92:3113-3121 (1995).
Strauss et al., *J. Nucl. Med.* 41 (5 Suppl.):149P (2000).
Sugihara et al., *Blood* 80:2634-2642 (1992).
Sun et al., *Thromb. Res.* 69:289-296 (1993).
Szoka, et al., *Proc. Natl. Acad. Sci.* 75:4194 (1978).
Tait et al., *J. Biol. Chem.* 264:7944-7949 (1989).
Thiagarajan and Tait, *J. Biol. Chem.* 265:17420-17423 (1990).
Van Heerde et al., *Arterioscler. Thromb.* 14:824-830 (1994).
Van Ryn-McKenna et al., *Thromb. Haemost.* 69:227-230 (1993).
Veronese et al., *Biomaterials* 22:405 (2001).
Fukunaga et al., *Endocrinol.* 115:757 (1984).
Green et al., *Am. J. Hematol.* 23:317 (1986).
Haupt et al., *Crit. Care Med.* 19:1339-1347 (1991).
Haut et al., *J. Lab. Clin. Med.* 82:44-53 (1973).
Heathcote et al., *N. Engl. J. Med.* 343:1673-1680 (2000).
Hebbel et al., *Abstract. Clin. Res.* 41:762A (1993).
Hermanson, *Bioconj Tech.* New York, Academic Press (1996), pp. 173-176.
Kang et al., *Trends Cardiovasc. Med.* 9:92-102 (1999).
Kaplan et al., *Blood* 57:199-202 (1981).
Kim et al., *Biochim. Biophys. Acta* 728:339 (1983).
D'Amico et al., FASEB J. vol. 14, pp. 1867-1869, 2000.
Robinson et al., "Optimizing the Stability of Single Chain Proteins by Linker Length and Composition Mutagenesis", Proc. Nat. Acad. Sci. USA, vol. 95, pp. 5929-5934, 1998.
Gerke et al., "Annexins:From Structure to Function", Physiol. Rev, bol. 82, pp. 331-371, 2002.
D'Amico et al., FASEB J, Express article 10.1096/99-0602fje, 2000.

* cited by examiner

SEQUENCE LISTING

```
<160> NUMBER OF SEQ ID NOS: 9

<210> SEQ ID NO 1
<211> LENGTH: 957
<212> TYPE: DNA
<213> ORGANISM: Homo sapiens

<400> SEQUENCE: 1
gcacaggttc tcagaggcac tgtgactgac ttccctggat ttgatgagcg ggctgatgca      60
gaaactcttc ggaaggctat gaaaggcttg ggcacagatg aggagagcat cctgactctg     120
ttgacatccc gaagtaatgc tcagcgccag gaaatctctg cagcttttaa gactctgttt     180
ggcagggatc ttctggatga cctgaaatca gaactaactg gaaaatttga aaaattaatt     240
gtggctctga tgaaaccctc tcggctttat gatgcttatg aactgaaaca tgccttgaag     300
ggagctggaa caaatgaaaa agtactgaca gaaattattg cttcaaggac acctgaagaa     360
ctgagagcca tcaaacaagt ttatgaagaa gaatatggct caagcctgga agatgacgtg     420
```

```
gtgggggaca cttcagggta ctaccagcgg atgttggtgg ttctccttca ggctaacaga    480
gaccctgatg ctggaattga tgaagctcaa gttgaacaag atgctcaggc tttatttcag    540
gctggagaac ttaaatgggg gacagatgaa gaaaagttta tcaccatctt tggaacacga    600
agtgtgtctc atttgagaaa ggtgtttgac aagtacatga ctatatcagg atttcaaatt    660
gaggaaacca ttgaccgcga gacttctggc aatttagagc aactactcct tgctgttgtg    720
aaatctattc gaagtatacc tgcctacctt gcagagaccc tctattatgc tatgaaggga    780
gctgggacag atgatcatac cctcatcaga gtcatggttt ccaggagtga gattgatctg    840
tttaacatca ggaaggagtt taggaagaat tttgccacct ctctttattc catgattaag    900
ggagatacat ctggggacta taagaaagct cttctgctgc tctgtggaga agatgac      957
```

```
<210> SEQ ID NO 2
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 2
```

```
gca cag gtt ctc aga ggc act gtg act gac ttc cct gga ttt gat gag       48
Ala Gln Val Leu Arg Gly Thr Val Thr Asp Phe Pro Gly Phe Asp Glu
1               5                   10                  15 cgg gct gat gca gaa act ctt cgg aag gct atg aaa ggc ttg ggc aca       96
Arg Ala Asp Ala Glu Thr Leu Arg Lys Ala Met Lys Gly Leu Gly Thr
            20                  25                  30 gat gag gag agc atc ctg act ctg ttg aca tcc cga agt aat gct cag      144
Asp Glu Glu Ser Ile Leu Thr Leu Leu Thr Ser Arg Ser Asn Ala Gln
        35                  40                  45 cgc cag gaa atc tct gca gct ttt aag act ctg ttt ggc agg gat ctt      192
Arg Gln Glu Ile Ser Ala Ala Phe Lys Thr Leu Phe Gly Arg Asp Leu
    50                  55                  60 ctg gat gac ctg aaa tca gaa cta act gga aaa ttt gaa aaa tta att      240
Leu Asp Asp Leu Lys Ser Glu Leu Thr Gly Lys Phe Glu Lys Leu Ile
65                  70                  75                  80 gtg gct ctg atg aaa ccc tct cgg ctt tat gat gct tat gaa ctg aaa      288
Val Ala Leu Met Lys Pro Ser Arg Leu Tyr Asp Ala Tyr Glu Leu Lys
                85                  90                  95 cat gcc ttg aag gga gct gga aca aat gaa aaa gta ctg aca gaa att      336
His Ala Leu Lys Gly Ala Gly Thr Asn Glu Lys Val Leu Thr Glu Ile
            100                 105                 110 att gct tca agg aca cct gaa gaa ctg aga gcc atc aaa caa gtt tat      384
Ile Ala Ser Arg Thr Pro Glu Glu Leu Arg Ala Ile Lys Gln Val Tyr
        115                 120                 125 gaa gaa gaa tat ggc tca agc ctg gaa gat gac gtg gtg ggg gac act      432
Glu Glu Glu Tyr Gly Ser Ser Leu Glu Asp Asp Val Val Gly Asp Thr
    130                 135                 140 tca ggg tac tac cag cgg atg ttg gtg gtt ctc ctt cag gct aac aga      480
Ser Gly Tyr Tyr Gln Arg Met Leu Val Val Leu Leu Gln Ala Asn Arg
145                 150                 155                 160 gac cct gat gct gga att gat gaa gct caa gtt gaa caa gat gct cag      528
Asp Pro Asp Ala Gly Ile Asp Glu Ala Gln Val Glu Gln Asp Ala Gln
                165                 170                 175 gct tta ttt cag gct gga gaa ctt aaa tgg ggg aca gat gaa gaa aag      576
Ala Leu Phe Gln Ala Gly Glu Leu Lys Trp Gly Thr Asp Glu Glu Lys
            180                 185                 190 ttt atc acc atc ttt gga aca cga agt gtg tct cat ttg aga aag gtg      624
Phe Ile Thr Ile Phe Gly Thr Arg Ser Val Ser His Leu Arg Lys Val
```

```
                195                 200                 205
ttt gac aag tac atg act ata tca gga ttt caa att gag gaa acc att   672
Phe Asp Lys Tyr Met Thr Ile Ser Gly Phe Gln Ile Glu Glu Thr Ile
    210                 215                 220 gac cgc gag act tct ggc aat tta gag caa cta ctc ctt gct gtt gtg   720
Asp Arg Glu Thr Ser Gly Asn Leu Glu Gln Leu Leu Leu Ala Val Val
225                 230                 235                 240 aaa tct att cga agt ata cct gcc tac ctt gca gag acc ctc tat tat   768
Lys Ser Ile Arg Ser Ile Pro Ala Tyr Leu Ala Glu Thr Leu Tyr Tyr
                245                 250                 255 gct atg aag gga gct ggg aca gat gat cat acc ctc atc aga gtc atg   816
Ala Met Lys Gly Ala Gly Thr Asp Asp His Thr Leu Ile Arg Val Met
            260                 265                 270 gtt tcc agg agt gag att gat ctg ttt aac atc agg aag gag ttt agg   864
Val Ser Arg Ser Glu Ile Asp Leu Phe Asn Ile Arg Lys Glu Phe Arg
        275                 280                 285 aag aat ttt gcc acc tct ctt tat tcc atg att aag gga gat aca tct   912
Lys Asn Phe Ala Thr Ser Leu Tyr Ser Met Ile Lys Gly Asp Thr Ser
    290                 295                 300 ggg gac tat aag aaa gct ctt ctg ctg ctc tgt gga gaa gat gac       957
Gly Asp Tyr Lys Lys Ala Leu Leu Leu Leu Cys Gly Glu Asp Asp
305                 310                 315
```

<210> SEQ ID NO 3
<211> LENGTH: 319
<212> TYPE: PRT
<213> ORGANISM: Homo sapiens

<400> SEQUENCE: 3

```
Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
                20                  25                  30

Asp Glu Glu Ser Ile Leu Thr Leu Leu Thr Ser Arg Ser Asn Ala Gln
            35                  40                  45

Arg Gln Glu Ile Ser Ala Ala Phe Lys Thr Leu Phe Gly Arg Asp Leu
        50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
210                 215                 220
```

```
Asp Arg Glu Thr Ser Gly Asn Leu Glu Gln Leu Leu Ala Val Val
225                 230                 235                 240

Lys Ser Ile Arg Ser Ile Pro Ala Tyr Leu Ala Glu Thr Leu Tyr Tyr
            245                 250                 255

Ala Met Lys Gly Ala Gly Thr Asp Asp His Thr Leu Ile Arg Val Met
        260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Cys Gly Glu Asp Asp
305                 310                 315

<210> SEQ ID NO 4
<211> LENGTH: 2022
<212> TYPE: DNA
<213> ORGANISM: Artificial sequence
<220> FEATURE:
<223> OTHER INFORMATION: modified annexin gene
<220> FEATURE:
<221> NAME/KEY: Unsure
<222> LOCATION: (45)..(45)
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: Unsure
<222> LOCATION: (1003)..(1005)
<220> FEATURE:
<221> NAME/KEY: misc_feature
<222> LOCATION: (1003)..(1005)
<223> OTHER INFORMATION: n is a, c, g, or t
<220> FEATURE:
<221> NAME/KEY: Unsure
<222> LOCATION: (1054)..(1056)
<220> FEATURE:
<221> NAME/KEY: misc_feature
<222> LOCATION: (1054)..(1056)
<223> OTHER INFORMATION: n is a, c, g, or t

<400> SEQUENCE: 4
atggactaca aagacgatga cgacaagctt gcggccgcga attcngcaca ggttctcaga      60
ggcactgtga ctgacttccc tggatttgat gagcgggctg atgcagaaac tcttcggaag     120
gctatgaaag gcttgggcac agatgaggag agcatcctga ctctgttgac atcccgaagt     180
aatgctcagc gccaggaaat ctctgcagct tttaagactc tgtttggcag ggatcttctg     240
gatgacctga atcagaact aactggaaaa tttgaaaaat taattgtggc tctgatgaaa      300
ccctctcggc tttatgatgc ttatgaactg aaacatgcct tgaagggagc tggaacaaat     360
gaaaaagtac tgacagaaat tattgcttca aggacacctg aagaactgag agccatcaaa     420
caagtttatg aagaagaata tggctcaagc ctggaagatg acgtggtggg ggacacttca     480
gggtactacc agcggatgtt ggtggttctc cttcaggcta acagagaccc tgatgctgga     540
attgatgaag ctcaagttga acaagatgct caggctttat ttcaggctgg agaacttaaa     600
tgggggacag atgaagaaaa gtttatcacc atctttggaa cacgaagtgt gtctcatttg     660
agaaaggtgt ttgacaagta catgactata tcaggatttc aaattgagga aaccattgac     720
cgcgagactt ctggcaattt agagcaacta ctccttgctg ttgtgaaatc tattcgaagt     780
atacctgcct accttgcaga gaccctctat tatgctatga agggagctgg gacagatgat     840
cataccctca tcagagtcat ggtttccagg agtgagattg atctgtttaa catcaggaag     900
```

```
gagtttagga agaattttgc cacctctctt tattccatga ttaagggaga tacatctggg   960
gactataaga aagctcttct gctgctctgt ggagaagatg acnnnagatc tcgatcgggc  1020
ctggaggtgc tgttccaggg ccccggaagt actnnngcac aggttctcag aggcactgtg  1080
actgacttcc ctggatttga tgagcgggct gatgcagaaa ctcttcggaa ggctatgaaa  1140
ggcttgggca cagatgagga gagcatcctg actctgttga catcccgaag taatgctcag  1200
cgccaggaaa tctctgcagc ttttaagact ctgtttggca gggatcttct ggatgacctg  1260
aaatcagaac taactggaaa atttgaaaaa ttaattgtgg ctctgatgaa accctctcgg  1320
ctttatgatg cttatgaact gaaacatgcc ttgaagggag ctggaacaaa tgaaaaagta  1380
ctgacagaaa ttattgcttc aaggacacct gaagaactga gagccatcaa acaagtttat  1440
gaagaagaat atggctcaag cctggaagat gacgtggtgg gggacacttc agggtactac  1500
cagcggatgt tggtggttct ccttcaggct aacagagacc ctgatgctgg aattgatgaa  1560
gctcaagttg aacaagatgc tcaggcttta tttcaggctg agaacttaa atgggggaca  1620 gatgaagaaa agtttatcac catctttgga acacgaagtg tgtctcattt gagaaaggtg  1680
tttgacaagt acatgactat atcaggattt caaattgagg aaaccattga ccgcgagact  1740
tctggcaatt tagagcaact actccttgct gttgtgaaat ctattcgaag tatacctgcc  1800
taccttgcag agaccctcta ttatgctatg aagggagctg ggacagatga tcataccctc  1860
atcagagtca tggtttccag gagtgagatt gatctgttta acatcaggaa ggagtttagg  1920
aagaattttg ccacctctct ttattccatg attaagggag atacatctgg ggactataag  1980
aaagctcttc tgctgctctg tggagaagat gactaataat aa                    2022

<210> SEQ ID NO 5
<211> LENGTH: 2022
<212> TYPE: DNA
<213> ORGANISM: Artificial sequence
<220> FEATURE:
<223> OTHER INFORMATION: modified annexin gene
<220> FEATURE:
<221> NAME/KEY: CDS
<222> LOCATION: (1)..(2022)
<220> FEATURE:
<221> NAME/KEY: Unsure
<222> LOCATION: (45)..(45)
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: Unsure
<222> LOCATION: (1003)..(1005)
<220> FEATURE:
<221> NAME/KEY: misc_feature
<222> LOCATION: (1003)..(1005)
<223> OTHER INFORMATION: n is a, c, g, or t
<220> FEATURE:
<221> NAME/KEY: Unsure
<222> LOCATION: (1051)..(1053)
<220> FEATURE:
<221> NAME/KEY: Unsure
<222> LOCATION: (1054)..(1056)
<220> FEATURE:
<221> NAME/KEY: misc_feature
<222> LOCATION: (1054)..(1056)
<223> OTHER INFORMATION: n is a, c, g, or t

<400> SEQUENCE: 5 atg gac tac aaa gac gat gac gac aag ctt gcg gcc gcg aat tcn gca   48
Met Asp Tyr Lys Asp Asp Asp Asp Lys Leu Ala Ala Ala Asn Xaa Ala
1               5                   10                  15
```

```
cag gtt ctc aga ggc act gtg act gac ttc cct gga ttt gat gag cgg       96
Gln Val Leu Arg Gly Thr Val Thr Asp Phe Pro Gly Phe Asp Glu Arg
         20                  25                  30 gct gat gca gaa act ctt cgg aag gct atg aaa ggc ttg ggc aca gat      144
Ala Asp Ala Glu Thr Leu Arg Lys Ala Met Lys Gly Leu Gly Thr Asp
             35                  40                  45 gag gag agc atc ctg act ctg ttg aca tcc cga agt aat gct cag cgc      192
Glu Glu Ser Ile Leu Thr Leu Leu Thr Ser Arg Ser Asn Ala Gln Arg
 50                  55                  60 cag gaa atc tct gca gct ttt aag act ctg ttt ggc agg gat ctt ctg      240
Gln Glu Ile Ser Ala Ala Phe Lys Thr Leu Phe Gly Arg Asp Leu Leu
 65                  70                  75                  80 gat gac ctg aaa tca gaa cta act gga aaa ttt gaa aaa tta att gtg      288
Asp Asp Leu Lys Ser Glu Leu Thr Gly Lys Phe Glu Lys Leu Ile Val
                 85                  90                  95 gct ctg atg aaa ccc tct cgg ctt tat gat gct tat gaa ctg aaa cat      336
Ala Leu Met Lys Pro Ser Arg Leu Tyr Asp Ala Tyr Glu Leu Lys His
            100                 105                 110 gcc ttg aag gga gct gga aca aat gaa aaa gta ctg aca gaa att att      384
Ala Leu Lys Gly Ala Gly Thr Asn Glu Lys Val Leu Thr Glu Ile Ile
        115                 120                 125 gct tca agg aca cct gaa gaa ctg aga gcc atc aaa caa gtt tat gaa      432
Ala Ser Arg Thr Pro Glu Glu Leu Arg Ala Ile Lys Gln Val Tyr Glu
    130                 135                 140 gaa gaa tat ggc tca agc ctg gaa gat gac gtg gtg ggg gac act tca      480
Glu Glu Tyr Gly Ser Ser Leu Glu Asp Asp Val Val Gly Asp Thr Ser
145                 150                 155                 160 ggg tac tac cag cgg atg ttg gtg gtt ctc ttc agg gct aac aga gac      528
Gly Tyr Tyr Gln Arg Met Leu Val Val Leu Leu Gln Ala Asn Arg Asp
                165                 170                 175 cct gat gct gga att gat gaa gct caa gtt gaa caa gat gct cag gct      576
Pro Asp Ala Gly Ile Asp Glu Ala Gln Val Glu Gln Asp Ala Gln Ala
            180                 185                 190 tta ttt cag gct gga gaa ctt aaa tgg ggg aca gat gaa gaa aag ttt      624
Leu Phe Gln Ala Gly Glu Leu Lys Trp Gly Thr Asp Glu Glu Lys Phe
        195                 200                 205 atc acc atc ttt gga aca cga agt gtg tct cat ttg aga aag gtg ttt      672
Ile Thr Ile Phe Gly Thr Arg Ser Val Ser His Leu Arg Lys Val Phe
    210                 215                 220 gac aag tac atg act ata tca gga ttt caa att gag gaa acc att gac      720
Asp Lys Tyr Met Thr Ile Ser Gly Phe Gln Ile Glu Glu Thr Ile Asp
225                 230                 235                 240 cgc gag act tct ggc aat tta gag caa cta ctc ctt gct gtt gtg aaa      768
Arg Glu Thr Ser Gly Asn Leu Glu Gln Leu Leu Leu Ala Val Val Lys
                245                 250                 255 tct att cga agt ata cct gcc tac ctt gca gag acc ctc tat tat gct      816
Ser Ile Arg Ser Ile Pro Ala Tyr Leu Ala Glu Thr Leu Tyr Tyr Ala
            260                 265                 270 atg aag gga gct ggg aca gat gat cat acc ctc atc aga gtc atg gtt      864
Met Lys Gly Ala Gly Thr Asp Asp His Thr Leu Ile Arg Val Met Val
        275                 280                 285 tcc agg agt gag att gat ctg ttt aac atc agg aag gag ttt agg aag      912
Ser Arg Ser Glu Ile Asp Leu Phe Asn Ile Arg Lys Glu Phe Arg Lys
    290                 295                 300 aat ttt gcc acc tct ctt tat tcc atg att aag gga gat aca tct ggg      960
Asn Phe Ala Thr Ser Leu Tyr Ser Met Ile Lys Gly Asp Thr Ser Gly
305                 310                 315                 320 gac tat aag aaa gct ctt ctg ctg ctc tgt gga gaa gat gac nnn aga     1008
Asp Tyr Lys Lys Ala Leu Leu Leu Leu Cys Gly Glu Asp Asp Xaa Arg
```

-continued

```
                  325                 330                 335
tct cga tcg ggc ctg gag gtg ctg ttc cag ggc ccc gga agt act nnn    1056
Ser Arg Ser Gly Leu Glu Val Leu Phe Gln Gly Pro Gly Ser Thr Xaa
            340                 345                 350 gca cag gtt ctc aga ggc act gtg act gac ttc cct gga ttt gat gag    1104
Ala Gln Val Leu Arg Gly Thr Val Thr Asp Phe Pro Gly Phe Asp Glu
        355                 360                 365 cgg gct gat gca gaa act ctt cgg aag gct atg aaa ggc ttg ggc aca    1152
Arg Ala Asp Ala Glu Thr Leu Arg Lys Ala Met Lys Gly Leu Gly Thr
    370                 375                 380 gat gag gag agc atc ctg act ctg ttg aca tcc cga agt aat gct cag    1200
Asp Glu Glu Ser Ile Leu Thr Leu Leu Thr Ser Arg Ser Asn Ala Gln
385                 390                 395                 400 cgc cag gaa atc tct gca gct ttt aag act ctg ttt ggc agg gat ctt    1248
Arg Gln Glu Ile Ser Ala Ala Phe Lys Thr Leu Phe Gly Arg Asp Leu
                405                 410                 415 ctg gat gac ctg aaa tca gaa cta act gga aaa ttt gaa aaa tta att    1296
Leu Asp Asp Leu Lys Ser Glu Leu Thr Gly Lys Phe Glu Lys Leu Ile
            420                 425                 430 gtg gct ctg atg aaa ccc tct cgg ctt tat gat gct tat gaa ctg aaa    1344
Val Ala Leu Met Lys Pro Ser Arg Leu Tyr Asp Ala Tyr Glu Leu Lys
        435                 440                 445 cat gcc ttg aag gga gct gga aca aat gaa aaa gta ctg aca gaa att    1392
His Ala Leu Lys Gly Ala Gly Thr Asn Glu Lys Val Leu Thr Glu Ile
    450                 455                 460 att gct tca agg aca cct gaa gaa ctg aga gcc atc aaa caa gtt tat    1440
Ile Ala Ser Arg Thr Pro Glu Glu Leu Arg Ala Ile Lys Gln Val Tyr
465                 470                 475                 480 gaa gaa gaa tat ggc tca agc ctg gaa gat gac gtg gtg ggg gac act    1488
Glu Glu Glu Tyr Gly Ser Ser Leu Glu Asp Asp Val Val Gly Asp Thr
                485                 490                 495 tca ggg tac tac cag cgg atg ttg gtg gtt ctc ttc agg ctg aac aga    1536
Ser Gly Tyr Tyr Gln Arg Met Leu Val Val Leu Leu Gln Ala Asn Arg
            500                 505                 510 gac cct gat gct gga att gat gaa gct caa gtt gaa caa gat gct cag    1584
Asp Pro Asp Ala Gly Ile Asp Glu Ala Gln Val Glu Gln Asp Ala Gln
        515                 520                 525 gct tta ttt cag gct gga gaa ctt aaa tgg ggg aca gat gaa gaa aag    1632
Ala Leu Phe Gln Ala Gly Glu Leu Lys Trp Gly Thr Asp Glu Glu Lys
    530                 535                 540 ttt atc acc atc ttt gga aca cga agt gtg tct cat ttg aga aag gtg    1680
Phe Ile Thr Ile Phe Gly Thr Arg Ser Val Ser His Leu Arg Lys Val
545                 550                 555                 560 ttt gac aag tac atg act ata tca gga ttt caa att gag gaa acc att    1728
Phe Asp Lys Tyr Met Thr Ile Ser Gly Phe Gln Ile Glu Glu Thr Ile
                565                 570                 575 gac cgc gag act tct ggc aat tta gag caa cta ctc ctt gct gtt gtg    1776
Asp Arg Glu Thr Ser Gly Asn Leu Glu Gln Leu Leu Leu Ala Val Val
            580                 585                 590 aaa tct att cga agt ata cct gcc tac ctt gca gag acc ctc tat tat    1824
Lys Ser Ile Arg Ser Ile Pro Ala Tyr Leu Ala Glu Thr Leu Tyr Tyr
        595                 600                 605 gct atg aag gga gct ggg aca gat gat cat acc ctc atc aga gtc atg    1872
Ala Met Lys Gly Ala Gly Thr Asp Asp His Thr Leu Ile Arg Val Met
    610                 615                 620 gtt tcc agg agt gag att gat ctg ttt aac atc agg aag gag ttt agg    1920
Val Ser Arg Ser Glu Ile Asp Leu Phe Asn Ile Arg Lys Glu Phe Arg
625                 630                 635                 640 aag aat ttt gcc acc tct ctt tat tcc atg att aag gga gat aca tct    1968
```

-continued

```
Lys Asn Phe Ala Thr Ser Leu Tyr Ser Met Ile Lys Gly Asp Thr Ser
                645                 650                 655 ggg gac tat aag aaa gct ctt ctg ctg ctc tgt gga gaa gat gac taa      2016
Gly Asp Tyr Lys Lys Ala Leu Leu Leu Leu Cys Gly Glu Asp Asp
            660                 665                 670 taa taa                                                              2022

<210> SEQ ID NO 6
<211> LENGTH: 671
<212> TYPE: PRT
<213> ORGANISM: Artificial sequence
<220> FEATURE:
<221> NAME/KEY: misc_feature
<222> LOCATION: (15)..(15)
<223> OTHER INFORMATION: The 'Xaa' at location 15 stands for Ser.
<220> FEATURE:
<221> NAME/KEY: misc_feature
<222> LOCATION: (335)..(335)
<223> OTHER INFORMATION: The 'Xaa' at location 335 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (352)..(352)
<223> OTHER INFORMATION: The 'Xaa' at location 352 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: modified annexin gene

<400> SEQUENCE: 6

Met Asp Tyr Lys Asp Asp Asp Lys Leu Ala Ala Ala Asn Xaa Ala
1               5                   10                  15

Gln Val Leu Arg Gly Thr Val Thr Asp Phe Pro Gly Phe Asp Glu Arg
            20                  25                  30

Ala Asp Ala Glu Thr Leu Arg Lys Ala Met Lys Gly Leu Gly Thr Asp
        35                  40                  45

Glu Glu Ser Ile Leu Thr Leu Leu Thr Ser Arg Ser Asn Ala Gln Arg
    50                  55                  60

Gln Glu Ile Ser Ala Ala Phe Lys Thr Leu Phe Gly Arg Asp Leu Leu
65                  70                  75                  80

Asp Asp Leu Lys Ser Glu Leu Thr Gly Lys Phe Glu Lys Leu Ile Val
                85                  90                  95

Ala Leu Met Lys Pro Ser Arg Leu Tyr Asp Ala Tyr Glu Leu Lys His
            100                 105                 110

Ala Leu Lys Gly Ala Gly Thr Asn Glu Lys Val Leu Thr Glu Ile Ile
        115                 120                 125

Ala Ser Arg Thr Pro Glu Glu Leu Arg Ala Ile Lys Gln Val Tyr Glu
    130                 135                 140

Glu Glu Tyr Gly Ser Ser Leu Glu Asp Asp Val Val Gly Asp Thr Ser
145                 150                 155                 160

Gly Tyr Tyr Gln Arg Met Leu Val Val Leu Leu Gln Ala Asn Arg Asp
                165                 170                 175

Pro Asp Ala Gly Ile Asp Glu Ala Gln Val Glu Gln Asp Ala Gln Ala
            180                 185                 190

Leu Phe Gln Ala Gly Glu Leu Lys Trp Gly Thr Asp Glu Glu Lys Phe
        195                 200                 205

Ile Thr Ile Phe Gly Thr Arg Ser Val Ser His Leu Arg Lys Val Phe
    210                 215                 220

Asp Lys Tyr Met Thr Ile Ser Gly Phe Gln Ile Glu Glu Thr Ile Asp
225                 230                 235                 240
```

-continued

```
Arg Glu Thr Ser Gly Asn Leu Glu Gln Leu Leu Ala Val Val Lys
                245                 250                 255

Ser Ile Arg Ser Ile Pro Ala Tyr Leu Ala Glu Thr Leu Tyr Tyr Ala
                260                 265                 270

Met Lys Gly Ala Gly Thr Asp His Thr Leu Ile Arg Val Met Val
                275                 280                 285

Ser Arg Ser Glu Ile Asp Leu Phe Asn Ile Arg Lys Glu Phe Arg Lys
            290                 295                 300

Asn Phe Ala Thr Ser Leu Tyr Ser Met Ile Lys Gly Asp Thr Ser Gly
305                 310                 315                 320

Asp Tyr Lys Lys Ala Leu Leu Leu Cys Gly Glu Asp Xaa Arg
                325                 330                 335

Ser Arg Ser Gly Leu Glu Val Leu Phe Gln Gly Pro Gly Ser Thr Xaa
                340                 345                 350

Ala Gln Val Leu Arg Gly Thr Val Thr Asp Phe Pro Gly Phe Asp Glu
                355                 360                 365

Arg Ala Asp Ala Glu Thr Leu Arg Lys Ala Met Lys Gly Leu Gly Thr
370                 375                 380

Asp Glu Glu Ser Ile Leu Thr Leu Leu Thr Ser Arg Ser Asn Ala Gln
385                 390                 395                 400

Arg Gln Glu Ile Ser Ala Ala Phe Lys Thr Leu Phe Gly Arg Asp Leu
                405                 410                 415

Leu Asp Asp Leu Lys Ser Glu Leu Thr Gly Lys Phe Glu Lys Leu Ile
                420                 425                 430

Val Ala Leu Met Lys Pro Ser Arg Leu Tyr Asp Ala Tyr Glu Leu Lys
                435                 440                 445

His Ala Leu Lys Gly Ala Gly Thr Asn Glu Lys Val Leu Thr Glu Ile
                450                 455                 460

Ile Ala Ser Arg Thr Pro Glu Glu Leu Arg Ala Ile Lys Gln Val Tyr
465                 470                 475                 480

Glu Glu Glu Tyr Gly Ser Ser Leu Glu Asp Asp Val Val Gly Asp Thr
                485                 490                 495

Ser Gly Tyr Tyr Gln Arg Met Leu Val Val Leu Leu Gln Ala Asn Arg
                500                 505                 510

Asp Pro Asp Ala Gly Ile Asp Glu Ala Gln Val Glu Gln Asp Ala Gln
                515                 520                 525

Ala Leu Phe Gln Ala Gly Glu Leu Lys Trp Gly Thr Asp Glu Glu Lys
                530                 535                 540

Phe Ile Thr Ile Phe Gly Thr Arg Ser Val Ser His Leu Arg Lys Val
545                 550                 555                 560

Phe Asp Lys Tyr Met Thr Ile Ser Gly Phe Gln Ile Glu Glu Thr Ile
                565                 570                 575

Asp Arg Glu Thr Ser Gly Asn Leu Glu Gln Leu Leu Leu Ala Val Val
                580                 585                 590

Lys Ser Ile Arg Ser Ile Pro Ala Tyr Leu Ala Glu Thr Leu Tyr Tyr
                595                 600                 605

Ala Met Lys Gly Ala Gly Thr Asp Asp His Thr Leu Ile Arg Val Met
                610                 615                 620

Val Ser Arg Ser Glu Ile Asp Leu Phe Asn Ile Arg Lys Glu Phe Arg
625                 630                 635                 640

Lys Asn Phe Ala Thr Ser Leu Tyr Ser Met Ile Lys Gly Asp Thr Ser
                645                 650                 655
```

```
Gly Asp Tyr Lys Lys Ala Leu Leu Leu Leu Cys Gly Glu Asp Asp
            660                 665                 670

<210> SEQ ID NO 7
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(30)
<223> OTHER INFORMATION: primer

<400> SEQUENCE: 7
acctgagtag tcgccatggc acaggttctc                                    30

<210> SEQ ID NO 8
<211> LENGTH: 36
<212> TYPE: DNA
<213> ORGANISM: Artificial sequence
<220> FEATURE:
<223> OTHER INFORMATION: primer

<400> SEQUENCE: 8
cccgaattca cgttagtcat cttctccaca gagcag                             36

<210> SEQ ID NO 9
<211> LENGTH: 8
<212> TYPE: PRT
<213> ORGANISM: Artificial sequence
<220> FEATURE:
<223> OTHER INFORMATION: purification tag

<400> SEQUENCE: 9

Asp Tyr Leu Asp Asp Asp Asp Leu
1               5
```

MODIFIED ANNEXIN PROTEINS, AND METHODS AND COMPOSITIONS FOR USING THEM

CROSS-REFERENCE TO RELATED APPLICATIONS

This application is a continuation of U.S. application Ser. No. 10/080,370, now U.S. Pat. No. 6,962,903, "Modified Annexin Proteins and Methods for Preventing Thrombosis," filed Feb. 21, 2002, which claims priority from U.S. Provisional Application No. 60/270,402, "Optimizing the Annexin Molecule for Preventing Thrombosis," filed Feb. 21, 2001, and U.S. Provisional Application No. 60/332,582, "Modified Annexin Molecule for Preventing Thrombosis and Reperfusion Injury," filed Nov. 21, 2001, all of which are incorporated herein by reference.

FIELD OF THE INVENTION

The present invention relates generally to methods and compositions for treating thrombosis. More particularly, it relates to modified annexin proteins and methods for their use.

BACKGROUND OF THE INVENTION

Thrombosis—the formation, development, or presence of a blood clot (thrombus) in a blood vessel—is the most common severe medical disorder. The most frequent example of arterial thrombosis is coronary thrombosis, which leads to occlusion of the coronary arteries and often to myocardial infarction (heart attack). More than 1.3 million patients are admitted to the hospital for myocardial infarction each year in North America. The standard therapy is administration of a thrombolytic protein by infusion. Thrombolytic treatment of acute myocardial infarction is estimated to save 30 lives per 1000 patients treated; nevertheless the 30-day mortality for this disorder remains substantial (Mehta et al., Lancet 356: 449-454 (2000), incorporated herein by reference). It would be convenient to administer antithrombotic and thrombolytic agents by bolus injection, since they might be used before admission to hospital with additional benefit (Rawles, J. Am. Coll. Cardiol. 30:1181-1186 (1997), incorporated herein by reference). However, bolus injection (as opposed to a more gradual intravenous infusion) significantly increases the risk of cerebral hemorrhage (Mehta et al., 2000). The development of an agent able to prevent thrombosis and/or increase thrombolysis, without augmenting the risk of bleeding, would be desirable.

Unstable angina, caused by inadequate oxygen delivery to the heart due to coronary occlusion, is the most common cause of admission to hospital, with 1.5 million cases a year in the United States alone. When patients with occlusion of coronary arteries are treated with angioplasty and stenting, the use of an antibody against platelet gp IIb/IIIa decreases the likelihood of restenosis. However, the same antibody has shown no benefit in unstable angina without angioplasty, and a better method for preventing coronary occlusion in these patients is needed.

Another important example of arterial thrombosis is cerebral thrombosis. Intravenous recombinant tissue plasminogen activator (rtPA) is the only treatment for acute ischemic stroke that is approved by the Food and Drug Administration. The earlier it is administered the better (Ernst et al., Stroke 31:2552-2557 (2000), incorporated herein by reference). However, intravenous rtPA administration is associated with increased risk of intracerebral hemorrhage. Full-blown strokes are often preceded by transient ischemic attacks (TIA), and it is estimated that about 300,000 persons suffer TIA every year in the United States. It would be desirable to have a safe and effective agent that could be administered as a bolus and would for several days prevent recurrence of cerebral thrombosis without increasing the risk of cerebral hemorrhage. Thrombosis also contributes to peripheral arterial occlusion in diabetics and other patients, and an efficacious and safe antithrombotic agent for use in such patients is needed.

Venous thrombosis is a frequent complication of surgical procedures such as hip and knee arthroplasties. It would be desirable to prevent thrombosis without increasing hemorrhage into the field of operation. Similar considerations apply to venous thrombosis associated with pregnancy and parturition. Some persons are prone to repeated venous thrombotic events and are currently treated by antithrombotic agents such as coumarin-type drugs. The dose of such drugs must be titrated in each patient, and the margin between effective antithrombotic doses and those increasing hemorrhage is small. Having a treatment with better separation of antithrombotic activity from increased risk of bleeding is desirable. All of the recently introduced antithrombotic therapies, including ligands of platelet gp IIb/IIIa, low molecular weight heparins, and a pentasaccharide inhibitor of factor Xa, carry an increased risk of bleeding (Levine et al., Chest 119:108S-121S (2001), incorporated herein by reference). Hence there is a need to explore alternative strategies for preventing arterial and venous thrombosis without augmenting the risk of hemorrhage.

To inhibit the extension of arterial or venous thrombi without increasing hemorrhage, it is necessary to exploit potential differences between mechanisms involved in hemostasis and those involved in thrombosis in large blood vessels. Primary hemostatic mechanisms include the formation of platelet microaggregates, which plug capillaries and accumulate over damaged or activated endothelial cells in small blood vessels. Inhibitors of platelet aggregation, including agents suppressing the formation or action of thromboxane $A_2$, ligands of gp IIa/IIIb, and drugs acting on ADP receptors such as clopidogrel (Hallopeter, Nature 409:202-207 (2001), incorporated herein by reference), interfere with this process and therefore increase the risk of bleeding (Levine et al., 2001). In contrast to microaggregate formation, occlusion by an arterial or venous thrombus requires the continued recruitment and incorporation of platelets into the thrombus. To overcome detachment by shear forces in large blood vessels, platelets must be bound tightly to one another and to the fibrin network deposited around them.

Evidence has accumulated that the formation of tight macroaggregates of platelets is facilitated by a cellular and a humoral amplification mechanism, which reinforce each other. In the cellular mechanism, the formation of relatively loose microaggregates of platelets, induced by moderate concentrations of agonists such as ADP, thromboxane $A_2$, or collagen, is accompanied by the release from platelet α-granules of the 85-kD protein Gas6 (Angelillo-Scherrer et al., Nature Medicine 7:215-221 (2001), incorporated herein by reference). Binding of released Gas6 to receptor tyrosine kinases (Axl, Sky, Mer) expressed on the surface of platelets induces complete degranulation and the formation of tight macroaggregates of these cells. In the humoral amplification mechanism, a prothrombinase complex is formed on the surface of activated platelets and microvesicles. This generates thrombin and fibrin. Thrombin is itself a potent platelet activator and inducer of the release of Gas6 (Ishimoto and Nakano, *FEBS Lett.* 446:197-199 (2000), incorporated herein by reference). Fully activated platelets bind tightly to the fibrin network deposited around them. Histological observations show that both platelets and fibrin are necessary for the formation of a stable coronary thrombus in humans (Falk et al. Interrelationship between atherosclerosis and thrombosis. In Vanstraete et al. (editors), *Cardiovascular Thrombosis: Thrombocardiology and Thromboneurology*. Philadelphia: Lipincott-Raven Publishers (1998), pp. 45-58, incorporated herein by reference). Another platelet adhesion molecule, amphoterin, is translocated to the platelet surface during activation, and binds anionic phospholipid (Rouhainen et al., *Thromb. Hemost.* 84:1087-1094 (2000), incorporated herein by reference). Like Gas6, amphoterin could form a bridge during platelet aggregation.

The question arises whether it is possible to inhibit these amplification mechanisms but not the initial platelet aggregation step, thereby preventing thrombosis without increasing hemorrhage. The importance of cellular amplification has recently been established by studies of mice with targeted inactivation of Gas6 (Angelillo-Scherrer et al., 2001). The Gas6-/- mice were found to be protected against thrombosis and embolism induced by collagen and epinephrine. However, the Gas6-/- mice did not suffer from spontaneous hemorrhage and had normal bleeding after tail clipping. Furthermore, antibodies against Gas6 inhibited platelet aggregation in vitro as well as thrombosis induced in vivo by collagen and epinephrine. In principle, such antibodies, or ligands competing for Gas6 binding to receptor tyrosine kinases, might be used to inhibit thrombosis. However, in view of the potency of humoral amplification, it might be preferable to inhibit that step. Ideally such an inhibitor would also have additional suppressive activity on the Gas6-mediated cellular amplification mechanism.

A strategy for preventing both cellular and humoral amplification of platelet aggregation is provided by the annexins, a family of highly homologous antithrombotic proteins of which ten are expressed in several human tissues (Benz and Hofmann, *Biol. Chem.* 378:177-183 (1997), incorporated herein be reference). Annexins share the property of binding calcium and negatively charged phospholipids, both of which are required for blood coagulation. Under physiological conditions, negatively charged phospholipid is mainly supplied by phosphatidylserine (PS) in activated or damaged cell membranes. In intact cells, PS is confined to the inner leaflet of the plasma membrane bilayer and is not accessible on the surface. When platelets are activated, the amounts of PS accessible on their surface, and therefore the extent of annexin binding, are greatly increased (Sun et al., *Thrombosis Res.* 69:289-296 (1993), incorporated herein by reference). During activation of platelets, microvesicles are released from their surfaces, greatly increasing the surface area expressing anionic phospholipids with procoagulant activity (Merten et al., *Circulation* 99:2577-2582 (1999); Chow et al., *J. Lab. Clin. Med.* 135:66-72 (2000), both incorporated herein by reference). These may play an important role in the propagation of platelet-mediated arterial thrombi.

Proteins involved in the blood coagulation cascade (factors X, Xa, and Va) bind to membranes bearing PS on their surfaces, and to one another, forming a stable, tightly bound prothrombinase complex. Several annexins, including II, V, and VIII, bind PS with high affinity, thereby preventing the formation of a prothrombinase complex and exerting antithrombotic activity. Annexin V binds PS with very high affinity ($K_d$=1.7 nmol/L), greater than the affinity of factors X, Xa, and Va for negatively charged phospholipids (Thiagarajan and Tait, *J. Biol. Chem.* 265:17420-17423 (1990), incorporated herein by reference). Tissue factor-dependent blood coagulation on the surface of activated or damaged endothelial cells also requires surface expression of PS, and annexin V can inhibit this process (van Heerde et al., *Arterioscl. Thromb.* 14:824-830 (1994), incorporated herein by reference), although annexin is less effective in this activity than in inhibition of prothrombinase generation (Rao et al., *Thromb. Res.* 62:517-531 (1992), incorporated herein by reference).

The binding of annexin V to activated platelets and to damaged cells probably explains the selective retention of the protein in thrombi. This has been shown in experimental animal models of venous and arterial thrombosis (Stratton et al., *Circulation* 92:3113-3121 (1995); Thiagarajan and Benedict, *Circulation* 96:2339-2347 (1997), both incorporated herein by reference), and labeled annexin has been proposed for medical imaging of vascular thrombi in humans, with reduced noise and increased safety (Reno and Kasina, International Patent Application PCT/US95/07599 (WO 95/34315) (published Dec. 21, 1995), incorporated herein by reference). The binding to thrombi of a potent antithrombotic agent such as annexin V provides a strategy for preventing the extension or recurrence of thrombosis. Transient myocardial ischemia also increases annexin V binding (Dumont et al., *Circulation* 102:1564-1568 (2000), incorporated herein by reference). Annexin V imaging in humans has shown increased binding of the protein in transplanted hearts when endomyocardial biopsy has demonstrated vascular rejection (Acio et al., *J. Nuclear Med.* 41 (5 Suppl.):127P (2000), incorporated herein by reference). This binding is presumably due to PS exteriorized on the surface of damaged endothelial cells, as well as of apoptotic myocytes in hearts that are being rejected. It follows that administration of annexin after myocardial infarction should prevent the formation of prothrombotic complexes on both platelets and endothelial cells, thereby preventing the extension or recurrence of thrombosis. Annexin V binding is also augmented following cerebral hypoxia in humans (D'Arceuil et al., *Stroke* 2000: 2692-2700 (2000), incorporated herein by reference), which supports the hypothesis that administration of annexin following TIA may decrease the likelihood of developing a full-blown stroke.

Annexins have shown anticoagulant activity in several in vitro thrombin-dependent assays, as well as in experimental animal models of venous thrombosis (Romisch et al., *Thrombosis Res.* 61:93-104 (1991); Van Ryn-McKenna et al., *Thrombosis Hemostasis* 69:227-230 (1993), both incorporated herein by reference) and arterial thrombosis (Thiagarajan and Benedict, 1997). Remarkably, annexin in antithrombotic doses had no demonstrable effect on traditional ex vivo clotting tests in treated rabbits (Thiagarajan and Benedict, 1997) and did not significantly prolong bleeding times of treated rats (Van Ryn-McKenna et al., 1993). In treated rabbits annexin did not increase bleeding into a surgical incision (Thiagarajan and Benedict, 1997). Thus, uniquely among all the agents so far investigated, annexins exert antithrombotic activity without increasing hemorrhage. Annexins do not inhibit platelet aggregation triggered by agonists other than thrombin (van Heerde et al., 1994), and platelet aggregation is the primary hemostatic mechanism. In the walls of damaged blood vessels and in extravascular tissues, the tissue factor/VIIa complex also exerts hemostatic effects, and this system is less susceptible to inhibition by annexin V than is the prothrombinase complex (Rao et al., 1992). This is one argument for confining administered annexin V to the vascular compartment as far as possible; the risk of hemorrhage is likely to be reduced.

Despite such promising results for preventing thrombosis, a major problem associated with the therapeutic use of annexins is their short half-life in the circulation, estimated in experimental animals to be 5 to 15 minutes (Römisch et al., 1991; Stratton et al., 1995; Thiagarajan and Benedict, 1997); annexin V also has a short half-life in the circulation of humans (Strauss et al., *J. Nuclear Med.* 41 (5 Suppl.):149P (2000), incorporated herein by reference). Most of the annexin is lost into the urine, as expected of a 36 kDa protein (Thiagarajan and Benedict, 1997). There is a need, therefore, for a method of preventing annexin loss from the vascular compartment into the extravascular compartment and urine, thereby prolonging antithrombotic activity following a single injection.

SUMMARY OF THE INVENTION

The present invention provides compounds and methods for preventing arterial or venous thrombosis without increasing hemorrhage. A recombinant human annexin, preferably annexin V, is modified in such a way that its half-life in the vascular compartment is prolonged. This can be achieved in a variety of ways; three preferred embodiments are an annexin coupled to polyethylene glycol, a homopolymer or heteropolymer of annexin, and a fusion protein of annexin with another protein (e.g., the Fc portion of immunoglobulin). The modified annexin binds with high affinity to phosphatidylserine on the surface of activated platelets or injured cells, thereby preventing the binding of Gas6 as well as procoagulant proteins and the formation of a prothrombinase complex. Modified annexin therefore inhibits both the cellular and humoral mechanisms by which platelet aggregation is amplified, thereby preventing thrombosis.

In one embodiment, the present invention provides an isolated modified annexin protein containing an annexin protein, preferably annexin V, coupled to polyethylene glycol (PEG). Preferably, at least two PEG chains are coupled to a single annexin molecule, with each PEG having a molecular weight of at least 5 kDa, more preferably at least 10 kDa, and most preferably at least 15 kDa. In an alternative embodiment, an isolated modified annexin protein contains an annexin protein coupled to at least one additional protein, such as an additional annexin protein (forming a homodimer) or the Fc portion of immunoglobulin. The additional protein preferably has a molecular weight of at least 30 kDa. Also provided by the present invention are pharmaceutical compositions containing an antithrombotically effective amount of any of the modified annexin proteins of the invention.

In methods of the invention, the modified annexin is administered to a subject at risk of thrombosis in a pharmaceutical composition having an antithrombotically effective amount of any one of the modified annexin proteins of the present invention. For example, the pharmaceutical composition can be administered after an arterial thrombosis such as coronary thrombosis, cerebral thrombosis, or a transient cerebral ischemic attack. It can also be administered after a surgical operation associated with venous thrombosis. Additionally, it can be administered to subjects having conditions subject to arterial or venous thrombosis, such as diabetes, pregnancy, or parturition.

Also provided by the present invention are an isolated nucleic acid molecule encoding a homodimer of annexin, a recombinant molecule containing at least a portion of the nucleic acid molecule, and a recombinant cell containing at least a portion of the nucleic acid molecule. The recombinant cell is cultured under suitable conditions in a method of the invention to produce a homodimer of annexin.

The present invention also provides a method for screening for a modified annexin protein that modulates thrombosis using a thrombosis test system. The test system is contacted with a test modified annexin protein, after which the thrombolytic activity is assessed and compared with the activity of the system in the absence of the test modified annexin protein. Preferably, the activated partial thromboplastin time is measured. Also provided is a method for identifying a modified annexin protein by contacting activated platelets with a test modified annexin protein and assessing the platelet-binding and protein S-binding activity.

Also provided by the present invention is a method for in vivo screening for a modified annexin protein. In this method, a thrombosis animal model is contacted with a test modified annexin protein, after which the in vivo anticoagulation activity and increase in hemorrhage of the test modified annexin protein is assessed. The anticoagulation activity and time are compared with the anticoagulation activity and time of annexin, and the amount of hemorrhage is compared with hemorrhage in the animal model in the absence of the test modified annexin protein.

DETAILED DESCRIPTION OF THE INVENTION

Figure 1:
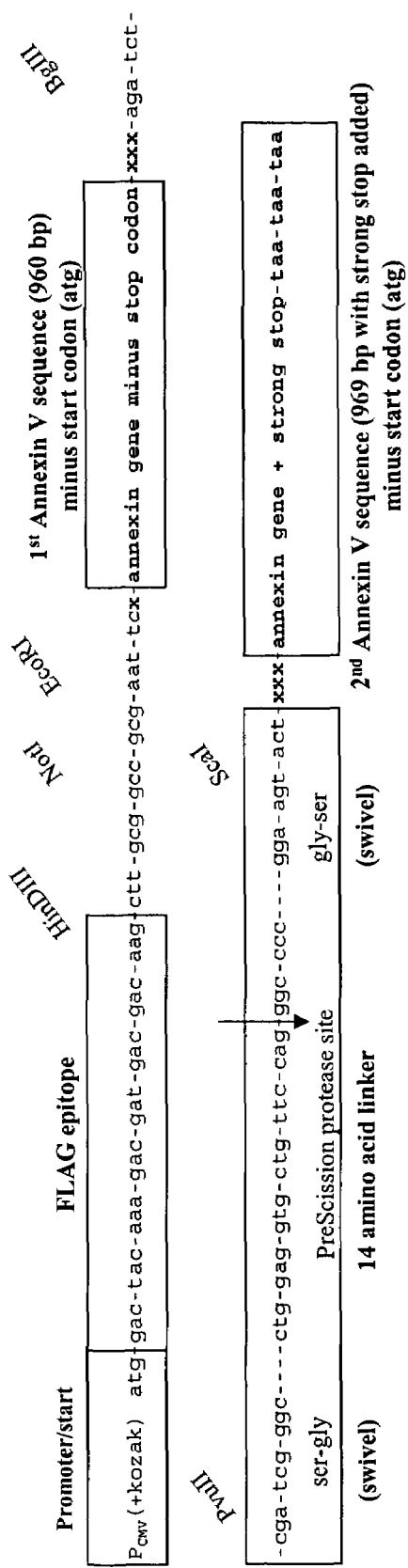
FIG. 1 shows a DNA construct SEQ ID NO: 4 for making a homodimer of annexin V.

The present invention provides compounds and methods for preventing thrombosis in mammals without increasing hemorrhage. The invention relies in part on the recognition that the primary mechanisms of platelet aggregation are different from the mechanisms of amplifying platelet aggregation, which are required for the formation of an arterial or venous thrombus. By inhibiting thrombus formation but not primary platelet aggregation, thrombosis can be prevented without increasing hemorrhage.

Compounds of the invention include any product containing annexin amino acid sequences that have been modified to increase the half-life of the product in humans or other mammals. Where "amino acid sequence" is recited herein to refer to an amino acid sequence of a naturally-occurring protein molecule, "amino acid sequence" and like terms, such as "polypeptide" or "protein," are not meant to limit the amino acid sequence to the complete, native amino acid sequence associated with the recited proteins. The annexins are a family of homologous phospholipid-binding membrane proteins, of which ten represent distinct gene products expressed in mammals (Benz and Hofmann, 1997). Crystallographic analysis has revealed a common tertiary structure for all the family members so far studied, exemplified by annexin V (Huber et al., *EMBO Journal* 9:3867 (1990), incorporated herein by reference). The core domain is a concave discoid structure that can be closely apposed to phospholipid membranes. It contains four subdomains, each consisting of a 70-amino-acid annexin repeat made up of five α-helices. The annexins also have a more hydrophilic tail domain that varies in length and amino acid sequence among the different annexins. The sequences of genes encoding annexins are well known (e.g., Funakoshi et al., *Biochemistry* 26:8087-8092 (1987) (annexin V), incorporated herein by reference).

In the present invention, annexin proteins are modified to increase their half-life in humans or other mammals. In a preferred embodiment, the annexin protein is annexin V. One suitable modification of annexin is an increase in its effective size, which prevents loss from the vascular compartment into the extravascular compartment and urine, thereby prolonging antithrombotic activity following a single injection. Any increase in effective size that maintains a sufficient binding affinity with phosphatidylserine is within the scope of the present invention.

In one embodiment of the invention, a modified annexin contains a recombinant human annexin protein coupled to polyethylene glycol (PEG) in such a way that the modified annexin is capable of performing the function of annexin in a phosphatidylserine (PS)-binding assay. The antithrombotic action of the intravenously administered annexin-PEG conjugate is prolonged as compared with that of the free annexin. The recombinant annexin protein coupled to PEG can be annexin V protein or another annexin protein.

PEG consists of repeating units of ethylene oxide that terminate in hydroxyl groups on either end of a linear or, in some cases, branched chain. The size and molecular weight of the coupled PEG chain depend upon the number of ethylene oxide units it contains, which can be selected. For the present invention, any size of PEG and number of PEG chains per annexin molecule can be used such that the half-life of the modified annexin is increased, relative to annexin, while preserving the function of binding of the modified molecule to PS. As stated above, sufficient binding includes binding that is diminished from that of the unmodified annexin, but still competitive with the binding of Gas6 and factors of the prothrombinase complex and therefore able to prevent thrombosis. The optimal molecular weight of the conjugated PEG varies with the number of PEG chains. In a most preferred embodiment, two PEG molecules of molecular weight of at least about 15 kDa each are coupled to each annexin molecule. The PEG molecules can be linear or branched. The calcium-dependent binding of annexins to PS is affected not only by the size of the coupled PEG molecules, but also the sites on the protein to which PEG is bound. Optimal selection ensures that desirable properties are retained. Selection of PEG attachment sites is facilitated by knowledge of the three-dimensional structure of the molecule and by mutational and crystallographic analyses of the interaction of the molecule with phospholipid membranes (Campos et al., *Biochemistry* 37:8004-8008 (1998), incorporated herein by reference).

In the area of drug delivery, PEG derivatives have been widely used in covalent attachment (referred to as pegylation) to proteins to enhance solubility, as well as to reduce immunogenicity, proteolysis, and kidney clearance. The superior clinical efficacy of recombinant products coupled to PEG is well established. For example, PEG-interferon alpha-2a administered once weekly is significantly more effective against hepatitis C virus than three weekly doses of the free interferon (Heathcote et al., *N. Engl. J. Med.* 343:1673-1680 (2000), incorporated herein by reference). Coupling to PEG has been used to prolong the half-life of recombinant proteins in vivo (Knauf et al., *J. Biol. Chem.* 266:2796-2804 (1988), incorporated herein by reference), as well as to prevent the enzymatic degradation of recombinant proteins and to decrease the immunogenicity sometimes observed with homologous products (references in Hermanson, Bioconjugate techniques. New York, Academic Press (1996), pp. 173-176, incorporated herein by reference).

In another embodiment of the invention, the modified annexin protein is a polymer of annexin proteins that has an increased effective size. It is believed that the increase in effective size results in prolonged half-life in the vascular compartment and prolonged antithrombotic activity. One such modified annexin is a dimer of annexin V. Another such polymer is the heterotetramer of annexin II with p11, a member of the S100 family of calcium-binding proteins. The binding of an S100 protein to an annexin increases the affinity of the annexin for $Ca^{2+}$. The annexin homopolymer or heterotetramer can be produced by bioconjugate methods or recombinant methods, and be administered by itself or in a PEG-conjugated form.

In another embodiment of the invention, recombinant annexin is expressed with, or chemically coupled to, another protein such as the Fc portion of immunoglobulin. Such expression or coupling increases the effective size of the molecule, preventing the loss of annexin from the vascular compartment and prolonging its anticoagulant action.

Preferably, a modified annexin protein of the invention is an isolated modified annexin protein. The modified annexin protein can contain annexin II, annexin V, or annexin VIII. In preferred embodiments, the protein is modified human annexin. In particularly preferred embodiments, the modified annexin contains recombinant human annexin. According to the present invention, an isolated or biologically pure protein is a protein that has been removed from its natural environment. As such, "isolated" and "biologically pure" do not necessarily reflect the extent to which the protein has been purified. An isolated modified annexin protein of the present invention can be obtained from its natural source, can be produced using recombinant DNA technology, or can be produced by chemical synthesis. As used herein, an isolated modified annexin protein can be a full-length modified protein or any homologue of such a protein. It can also be (e.g., for a pegylated protein) a modified full-length protein or a modified homologue of such a protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protein homologue of the present invention is from about 12 to about 18 nucleotides in length. There is no limit on the maximal size of such a nucleic acid molecule in that the nucleic acid molecule can include a portion of a gene, an entire gene, or multiple genes or portions thereof. Similarly, the minimal size of an annexin protein homologue or a modified annexin protein homologue of the present invention is from about 4 to about 6 amino acids in length, with preferred sizes depending on whether a full-length, multivalent (i.e., fusion protein having more than one domain, each of which has a function) protein, or functional portions of such proteins are desired. Annexin and modified annexin homologues of the present invention preferably have activity corresponding to the natural protein, such as being able to perform the activity of the annexin protein in preventing thrombus formation.

Annexin protein and modified annexin homologues can be the result of natural allelic variation or natural mutation. The protein homologues of the present invention can also be produced using techniques known in the art, including, but not limited to, direct modifications to the protein or modifications to the gene encoding the protein using, for example, classic or recombinant DNA techniques to effect random or targeted mutagenesis.

Also preferred is a modified annexin protein containing an amino acid sequence that is at least about 75%, more preferably at least about 80%, more preferably at least about 85%, more preferably at least about 90%, more preferably at least about 95%, and most preferably at least about 98% identical to amino acid sequence SEQ ID NO:3, SEQ ID NO:6, or a protein encoded by an allelic variant of a nucleic acid molecule encoding a protein containing any of these sequences. Methods to determine percent identities between amino acid sequences and between nucleic acid sequences are known to those skilled in the art. Preferred methods to determine percent identities between sequences include computer programs such as the GCG® Wisconsin package™ (available from Accelrys Corporation), the DNAsis™ program (available from Hitachi Software, San Bruno, Calif.), the Vector NTI Suite (available from Informax, Inc., North Bethesda, Md.), or the BLAST software available on the NCBI website.

In one embodiment, a preferred modified annexin protein includes an amino acid sequence of at least about 5 amino acids, preferably at least about 50 amino acids, more preferably at least about 100 amino acids, more preferably at least about 200 amino acids, more preferably at least about 250 amino acids, more preferably at least about 275 amino acids, more preferably at least about 300 amino acids, and most preferably at least about 319 amino acids or the full-length annexin protein, whichever is shorter. In another embodiment, preferred annexin proteins contain full-length proteins, i.e., proteins encoded by full-length coding regions, or post-translationally modified proteins thereof, such as mature proteins from which initiating methionine and/or signal sequences or "pro" sequences have been removed.

A fragment of a modified annexin protein of the present invention preferably contains at least about 5 amino acids, more preferably at least about 10 amino acids, more preferably at least about 15 amino acids, more preferably at least about 20 amino acids, more preferably at least about 25 amino acids, more preferably at least about 30 amino acids, more preferably at least about 35 amino acids, more preferably at least about 40 amino acids, more preferably at least about 45 amino acids, more preferably at least about 50 amino acids, more preferably at least about 55 amino acids, more preferably at least about 60 amino acids, more preferably at least about 65 amino acids, more preferably at least about 70 amino acids, more preferably at least about 75 amino acids, more preferably at least about 80 amino acids, more preferably at least about 85 amino acids, more preferably at least about 90 amino acids, more preferably at least about 95 amino acids, and even more preferably at least about 100 amino acids in length.

In one embodiment, a preferred isolated modified annexin protein of the present invention is a modified protein encoded by a nucleic acid molecule having the nucleic acid sequence SEQ ID NO:4 or by an allelic variant of a nucleic acid molecule having this sequence. Alternatively, the modified annexin protein contains a protein encoded by a nucleic acid molecule having the nucleic acid sequence SEQ ID NO:1 or by an allelic variant of a nucleic acid molecule having this sequence.

One embodiment of the present invention includes a non-native modified annexin protein encoded by a nucleic acid molecule that hybridizes under stringent hybridization conditions with an annexin gene. As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., *Molecular Cloning: A Laboratory Manual, Cold Spring Harbor Labs Press* (1989), incorporated herein by reference. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., *Anal. Biochem.* 138:267-284 (1984), incorporated herein by reference. In preferred embodiments, hybridization conditions will permit isolation of nucleic acid molecules having at least about 80% nucleic acid sequence identity with the nucleic acid molecule being used to probe. In more preferred embodiments, hybridization conditions will permit isolation of nucleic acid molecules having at least about 90% nucleic acid sequence identity with the nucleic acid molecule being used to probe. In more preferred embodiments, hybridization conditions will permit isolation of nucleic acid molecules having at least about 95% nucleic acid sequence identity with the nucleic acid molecule being used to probe.

A preferred modified annexin protein includes a protein encoded by a nucleic acid molecule that is at least about 50 nucleotides and that hybridizes under conditions that preferably allow about 20% base pair mismatch, more preferably under conditions that allow about 15% base pair mismatch, more preferably under conditions that allow about 10% base pair mismatch, more preferably under conditions that allow about 5% base pair mismatch, and even more preferably under conditions that allow about 2% base pair mismatch with a nucleic acid molecule selected from the group consisting of SEQ ID NO:1, SEQ ID NO:4, or a complement of either of these nucleic acid molecules.

As used herein, an annexin gene includes all nucleic acid sequences related to a natural annexin gene such as regulatory regions that control production of the annexin protein encoded by that gene (such as, but not limited to, transcription, translation or post-translation control regions) as well as the coding region itself. In one embodiment, an annexin gene includes the nucleic acid sequence SEQ ID NO:1. It should be noted that since nucleic acid sequencing technology is not entirely error-free, SEQ ID NO:1 (as well as other sequences presented herein), at best, represents an apparent nucleic acid sequence of the nucleic acid molecule encoding an annexin protein of the present invention.

In another embodiment, an annexin gene can be an allelic variant that includes a similar but not identical sequence to SEQ ID NO:1. An allelic variant of an annexin gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given human since the genome is diploid and/or among a population comprising two or more humans.

An isolated modified annexin protein of the present invention can be obtained from its natural source, can be produced using recombinant DNA technology, or can be produced by chemical synthesis. As used herein, an isolated modified annexin protein can contain a full-length protein or any homologue of such a protein. Examples of annexin and modified annexin homologues include annexin and modified annexin proteins in which amino acids have been deleted (e.g., a truncated version of the protein, such as a peptide or by a protein splicing reaction when an intein has been removed or two exteins are joined), inserted, inverted, substituted and/or derivatized (e.g., by glycosylation, phosphorylation, acetylation, methylation, myristylation, prenylation, palmitoylation, amidation and/or addition of glycerophosphatidyl inositol) such that the homologue includes at least one epitope capable of eliciting an immune response against an annexin protein. That is, when the homologue is administered to an animal as an immunogen, using techniques known to those skilled in the art, the animal will produce a humoral and/or cellular immune response against at least one epitope of an annexin protein. Annexin and modified annexin homologues can also be selected by their ability to selectively bind to immune serum. Methods to measure such activities are disclosed herein. Annexin and modified annexin homologues also include those proteins that are capable of performing the function of native annexin in a functional assay; that is, are capable of binding to phosphatidylserine or to activated platelets or exhibiting antithrombotic activity. Methods for such assays are described in the Examples section and elsewhere herein.

A modified annexin protein of the present invention may be identified by its ability to perform the function of an annexin protein in a functional assay. The phrase "capable of performing the function of that protein in a functional assay" means that the protein or modified protein has at least about 10% of the activity of the natural protein in the functional assay. In other preferred embodiments, it has at least about 20% of the activity of the natural protein in the functional assay. In other preferred embodiments, it has at least about 30% of the activity of the natural protein in the functional assay. In other preferred embodiments, it has at least about 40% of the activity of the natural protein in the functional assay. In other preferred embodiments, it has at least about 50% of the activity of the natural protein in the functional assay. In other preferred embodiments, the protein or modified protein has at least about 60% of the activity of the natural protein in the functional assay. In more preferred embodiments, the protein or modified protein has at least about 70% of the activity of the natural protein in the functional assay. In more preferred embodiments, the protein or modified protein has at least about 80% of the activity of the natural protein in the functional assay. In more preferred embodiments, the protein or modified protein has at least about 90% of the activity of the natural protein in the functional assay. Examples of functional assays are described herein.

An isolated protein of the present invention can be produced in a variety of ways, including recovering such a protein from a bacterium and producing such a protein recombinantly. One embodiment of the present invention is a method to produce an isolated modified annexin protein of the present invention using recombinant DNA technology. Such a method includes the steps of (a) culturing a recombinant cell containing a nucleic acid molecule encoding a modified annexin protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques.

Isolated proteins of the present invention are preferably retrieved in "substantially pure" form. As used herein, "substantially pure" refers to a purity that allows for the effective use of the protein in a functional assay.

Modified Annexin Nucleic Acid Molecules or Genes

Another embodiment of the present invention is an isolated nucleic acid molecule capable of hybridizing under stringent conditions with a gene encoding a modified annexin protein such as a homodimer of annexin V. Such a nucleic acid molecule is also referred to herein as a modified annexin nucleic acid molecule. Particularly preferred is an isolated nucleic acid molecule that hybridizes under stringent conditions with a modified annexin gene. The characteristics of such genes are disclosed herein. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a modified annexin gene includes all nucleic acid sequences related to a natural annexin gene, such as regulatory regions that control production of an annexin protein encoded by that gene (such as, but not limited to, transcriptional, translational, or post-translational control regions) as well as the coding region itself. A nucleic acid molecule of the present invention can be an isolated modified annexin nucleic acid molecule or a homologue thereof. A nucleic acid molecule of the present invention can include one or more regulatory regions, full-length or partial coding regions, or combinations thereof. The minimal size of a modified annexin nucleic acid molecule of the present invention is the minimal size capable of forming a stable hybrid under stringent hybridization conditions with a corresponding natural gene. Annexin nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning, etc.) or chemical synthesis. Isolated modified annexin nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the ability of the nucleic acid molecule to encode a modified annexin protein of the present invention or to form stable hybrids under stringent conditions with natural nucleic acid molecule isolates.

A modified annexin nucleic acid molecule homologue can be produced using a number of methods known to those skilled in the art (see, e.g., Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures, and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against an annexin protein and/ or to function in a clotting assay, or other functional assay), and/or by hybridization with isolated annexin-encoding nucleic acids under stringent conditions.

An isolated modified annexin nucleic acid molecule of the present invention can include a nucleic acid sequence that encodes at least one modified annexin protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a modified annexin protein.

One embodiment of the present invention is a modified annexin nucleic acid molecule that is capable of hybridizing under stringent conditions to a nucleic acid strand that encodes at least a portion of a modified annexin protein or a homologue thereof or to the complement of such a nucleic acid strand. A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand, that is represented by a SEQ ID NO, also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. Preferred is a modified annexin nucleic acid molecule that includes a nucleic acid sequence having at least about 65 percent, preferably at least about 70 percent, more preferably at least about 75 percent, more preferably at least about 80 percent, more preferably at least about 85 percent, more preferably at least about 90 percent and even more preferably at least about 95 percent homology with the corresponding region(s) of the nucleic acid sequence encoding at least a portion of a modified annexin protein. Particularly preferred is a modified annexin nucleic acid molecule capable of encoding a homodimer of an annexin protein or homologue thereof.

Preferred annexin nucleic acid molecules include SEQ ID NO:4 and an allelic variants of SEQ ID NO:4.

Knowing a nucleic acid molecule of a modified annexin protein of the present invention allows one skilled in the art to make copies of that nucleic acid molecule as well as to obtain a nucleic acid molecule including additional portions of annexin protein-encoding genes (e.g., nucleic acid molecules that include the translation start site and/or transcription and/ or translation control regions), and/or annexin nucleic acid molecule homologues. Knowing a portion of an amino acid sequence of an annexin protein of the present invention allows one skilled in the art to clone nucleic acid sequences encoding such an annexin protein. In addition, a desired modified annexin nucleic acid molecule can be obtained in a variety of ways including screening appropriate expression libraries with antibodies that bind to annexin proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used).

The present invention also includes nucleic acid molecules that are oligonucleotides capable of hybridizing, under stringent conditions, with complementary regions of other, preferably longer, nucleic acid molecules of the present invention that encode at least a portion of a modified annexin protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to modulate modified annexin production. Such therapeutic applications include the use of such oligonucleotides in, for example, antisense-, triplex formation-, ribozyme- and/or RNA drug-based technologies. The present invention, therefore, includes such oligonucleotides and methods to modulate the production of modified annexin proteins by use of one or more of such technologies.

Natural, Wild-Type Bacterial Cells and Recombinant Molecules and Cells

The present invention also includes a recombinant vector, which includes a modified annexin nucleic acid molecule of the present invention inserted into any vector capable of delivering the nucleic acid molecule into a host cell. Such a vector contains heterologous nucleic acid sequences, that is, nucleic acid sequences that are not naturally found adjacent to modified annexin nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of modified annexin nucleic acid molecules of the present invention. One type of recombinant vector, herein referred to as a recombinant molecule and described in more detail below, can be used in the expression of nucleic acid molecules of the present invention. Preferred recombinant vectors are capable of replicating in the transformed cell. Preferred nucleic acid molecules to include in recombinant vectors of the present invention are disclosed herein.

As heretofore disclosed, one embodiment of the present invention is a method to produce a modified annexin protein of the present invention by culturing a cell capable of expressing the protein under conditions effective to produce the protein, and recovering the protein. In an alternative embodiment, the method includes producing an annexin protein by culturing a cell capable of expressing the protein under conditions effective to produce the annexin protein, recovering the protein, and modifying the protein by coupling it to an agent that increases its effective size.

In a preferred embodiment, the cell to culture is a natural bacterial cell, and modified annexin is isolated from these cells. In another embodiment, a preferred cell to culture is a recombinant cell that is capable of expressing the modified annexin protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a host cell are disclosed herein.

Suitable host cells to transform include any cell that can be transformed and that can express the introduced modified annexin protein. Such cells are, therefore, capable of producing modified annexin proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal, and plant cells. Preferred host cells include bacterial cells, with *E. coli* cells being particularly preferred. Alternative preferred host cells are untransformed (wild-type) bacterial cells producing cognate modified annexin proteins, including attenuated strains with reduced pathogenicity, as appropriate.

A recombinant cell is preferably produced by transforming a host cell with one or more recombinant molecules, each comprising one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence that is capable of controlling the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to the art. Preferred transcription control sequences include those which function in bacterial, yeast, insect and mammalian cells, such as, but not limited to, tac, lac, tzp, trc, oxy-pro, omp/lpp, mmb, bacteriophage lambda (λ) (such as $\lambda p_L$ and $\lambda p_R$ and fusions that include such promoters), bacteriophage T7, T71ac, bacteriophage T3, bacteriophage SP6, bacteriophage SP01, metallothionein, alpha mating factor, *Pichia* alcohol oxidase, alphavirus subgenomic promoters (such as Sindbis virus subgenomic promoters), baculovirus, *Heliothis zea* insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an annexin protein. A preferred transcription control sequence is the Kozak strong promotor and initiation sequence.

Expression vectors of the present invention may also contain secretory signals (i.e., signal segment nucleic acid sequences) to enable an expressed annexin protein to be secreted from the cell that produces the protein. Suitable signal segments include an annexin protein signal segment or any heterologous signal segment capable of directing the secretion of an annexin protein, including fusion proteins, of the present invention. Preferred signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a modified annexin nucleic acid molecule of the present invention can enhance the stability during production, storage and/or use of the protein encoded by the nucleic acid molecule. Furthermore, a fusion segment can function as a tool to simplify purification of a modified annexin protein, such as to enable purification of the resultant fusion protein using affinity chromatography. A preferred fusion segment that can be used for protein purification is the 8-amino acid peptide sequence asp-tyr-lys-asp-asp-asp-asp-lys (SEQ ID NO:9).

A suitable fusion segment can be a domain of any size that has the desired function (e.g., increased stability and/or purification tool). It is within the scope of the present invention to use one or more fusion segments. Fusion segments can be joined to amino and/or carboxyl termini of an annexin protein. Another type of preferred fusion protein is a fusion protein wherein the fusion segment connects two or more annexin proteins or modified annexin proteins. Linkages between fusion segments and annexin proteins can be constructed to be susceptible to cleavage to enable straightforward recovery of the annexin or modified annexin proteins.

Fusion proteins are preferably produced by culturing a recombinant cell transformed with a fusion nucleic acid sequence that encodes a protein including the fusion segment attached to either the carboxyl and/or amino terminal end of an annexin protein.

A recombinant molecule of the present invention is a molecule that can include at least one of any nucleic acid molecule heretofore described operatively linked to at least one of any transcription control sequence capable of effectively regulating expression of the nucleic acid molecules in the cell to be transformed. A preferred recombinant molecule includes one or more nucleic acid molecules of the present invention, with those that encode one or more modified annexin proteins being particularly preferred. Preferred recombinant molecules of the present invention and their production are described in the Examples section. Similarly, a preferred recombinant cell includes one or more nucleic acid molecules of the present invention, with those that encode one or more modified annexin proteins. Preferred recombinant cells of the present invention include those disclosed in the Examples section.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce annexin or modified annexin proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an annexin or modified annexin protein. Such a medium is typically an aqueous medium comprising assimilable carbohydrate, nitrogen and phosphate sources, as well as appropriate salts, minerals, metals and other nutrients, such as vitamins. The medium may comprise complex, nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant modified annexin proteins may either remain within the recombinant cell; be secreted into the fermentation medium; be secreted into a space between two cellular membranes, such as the periplasmic space in $E.$ $coli$; or be retained on the outer surface of a cell or viral membrane. Methods to purify such proteins are disclosed in the Examples section.

Antibodies

The present invention also includes isolated anti-modified annexin antibodies and their use. An anti-modified annexin antibody is an antibody capable of selectively binding to a modified annexin protein. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protein against which the antibody was raised (i.e., to be able to distinguish that protein from unrelated components in a mixture). Binding affinities, commonly expressed as equilibrium association constants, typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immuno-electron microscopy; see, e.g., Sambrook et al., 1989.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Preferred antibodies are raised in response to proteins that are encoded, at least in part, by a modified annexin nucleic acid molecule of the present invention.

Anti-modified annexin antibodies of the present invention include antibodies raised in an animal administered a modified annexin. Anti-modified annexin antibodies of the present invention also include antibodies raised in an animal against one or more modified annexin proteins of the present invention that are then recovered from the cell using techniques known to those skilled in the art. Yet additional antibodies of the present invention are produced recombinantly using techniques as heretofore disclosed for modified annexin proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-modified annexin antibodies of the present invention have a variety of uses that are within the scope of the present invention. Anti-modified annexin antibodies can be used as tools to screen expression libraries and/or to recover desired proteins of the present invention from a mixture of proteins and other contaminants.

A preferred anti-modified annexin antibody of the present invention can selectively bind to a modified annexin protein.

Therapeutic Methods

Any of the above-described modified annexin proteins is used in methods of the invention to treat arterial or venous thrombosis caused by any medical procedure or condition. Generally, the therapeutic agents used in the invention are administered to an animal in an effective amount. Generally, an effective amount is an amount effective either (1) to reduce the symptoms of the disease sought to be treated or (2) to induce a pharmacological change relevant to treating the disease sought to be treated.

For thrombosis, an effective amount includes an amount effective to exert prolonged antithrombotic activity without substantially increasing the risk of hemorrhage or to increase the life expectancy of the affected animal. As used herein, prolonged antithrombotic activity refers to the time of activity of the modified annexin protein with respect to the time of activity of the same amount (molar) of an unmodified annexin protein. Preferably, antithrombotic activity is prolonged by at least about a factor of two, more preferably by at least about a factor of five, and most preferably by at least about a factor of ten. Preferably, the effective amount does not substantially increase the risk of hemorrhage compared with the hemorrhage risk of the same subject to whom the modified annexin has not been administered. Preferably, the hemorrhage risk is very small and, at most, below that provided by alternative antithrombotic treatments available in the prior art. Therapeutically effective amounts of the therapeutic agents can be any amount or dose sufficient to bring about the desired antithrombotic effect and depends, in part, on the condition, type, and location of the thrombus, the size and condition of the patient, as well as other factors known to those skilled in the art. The dosages can be given as a single dose, or as several doses, for example, divided over the course of several weeks.

Administration preferably occurs by bolus injection or by intravenous infusion, either after thrombosis to prevent further thrombosis or under conditions in which the subject is susceptible to or at risk of thrombosis.

The therapeutic agents of the present invention can be administered by any suitable means, including, for example, parenteral or local administration, such as intravenous or subcutaneous injection, or by aerosol. A therapeutic composition can be administered in a variety of unit dosage forms depending upon the method of administration. Preferred delivery methods for a therapeutic composition of the present invention include intravenous administration and local administration by, for example, injection. For particular modes of delivery, a therapeutic composition of the present invention can be formulated in an excipient of the present invention. A therapeutic reagent of the present invention can be administered to any animal, preferably to mammals, and more preferably to humans.

One suitable administration time occurs following coronary thrombosis, thereby preventing the recurrence of thrombosis without substantially increasing the risk of hemorrhage. Bolus injection of the modified annexin is preferably performed soon after thrombosis, e.g., before admission to hospital. The modified annexin can be administered in conjunction with a thrombolytic therapeutic such as tissue plasminogen activator, urokinase, or a bacterial enzyme.

Methods of use of modified annexin proteins of the present invention include methods to treat cerebral thrombosis, including overt cerebral thrombosis or transient cerebral ischemic attacks, by administering an effective amount of modified annexin protein to a patient in need thereof. Transient cerebral ischemic attacks frequently precede full-blown strokes. The modified annexin can also be administered to diabetic and other patients who are at increased risk for thrombosis in peripheral arteries. Accordingly, the present invention provides a method for reducing the risk of thrombosis in a patient having an increased risk for thrombosis including administering an effective amount of a modified annexin protein to a patient in need thereof. For an adult patient, the modified annexin can be administered intravenously or as a bolus in the dosage range of about 1 to about 100 mg.

The present invention also provides a method for decreasing the risk of venous thrombosis associated with some surgical procedures, such as hip and knee arthroplasties, by administering an effective amount of a modified annexin protein of the present invention to a patient in need thereof. The modified annexin treatment can prevent thrombosis without increasing hemorrhage into the operating field. In another embodiment, the present invention provides a method for preventing thrombosis associated with pregnancy and parturition without increasing hemorrhage, by administering an effective amount of a modified annexin protein of the present invention to a patient in need thereof. In a further embodiment, the present invention provides a method for the treatment of recurrent venous thrombosis, by administering an effective amount of a modified annexin protein of the present invention to a patient in need thereof. For an adult patient, the modified annexin can be administered intravenously as a bolus in the dosage range of about 1 to about 100 mg.

The present invention also provides a method of screening for a modified annexin protein that modulates thrombosis, by contacting a thrombosis test system with at least one test modified annexin protein under conditions permissive for thrombosis, and comparing the antithrombotic activity in the presence of the test modified annexin protein with the antithrombotic activity in the absence of the test modified annexin protein, wherein a change in the antithrombotic activity in the presence of the test modified annexin protein is indicative of a modified annexin protein that modulates thrombotic activity. In a preferred embodiment, the thrombosis test system is a system for measuring activated partial thromboplastin time. Also included within the scope of the present invention are modified annexin proteins that modulate thrombosis as identified by this method.

The present invention also provides a method for identifying a modified annexin protein for annexin activity, including contacting activated platelets with at least one test modified annexin protein under conditions permissive for binding, and comparing the test modified annexin-binding activity and protein S-binding activity of the platelets in the presence of the test modified annexin protein with the annexin-binding activity and protein S-binding activity in the presence of unmodified annexin protein, whereby a modified annexin protein with annexin activity may be identified. Also included within the scope of the invention are modified annexin proteins identified by the method.

In an additional embodiment, the present invention provides a method of screening for a modified annexin protein that modulates thrombosis, by contacting an in vivo thrombosis test system with at least one test modified annexin protein under conditions permissive for thrombosis, and comparing the antithrombotic activity in the presence of the test modified annexin protein with the antithrombotic activity in the absence of the test modified annexin protein. A change in the antithrombotic activity in the presence of the test modified annexin protein is indicative of a modified annexin protein that modulates thrombotic activity. Additionally, the time over which antithrombotic activity is sustained in the presence of the test modified annexin protein is compared with a time of antithrombotic activity in the presence of unmodified annexin to determine the prolongation of antithrombotic activity associated with the test modified annexin protein. The extent of hemorrhage in the presence of the test modified annexin protein is assessed, e.g., by measuring tail bleeding time, and compared with the extent of hemorrhage in the absence of the test modified annexin protein. In a preferred embodiment, the in vivo thrombosis test system is a mouse model of photochemically-induced thrombus in cremaster muscles. Also included within the scope of the present invention are modified annexin proteins that modulate thrombosis as identified by this method.

In a further embodiment, the therapeutic agents of the present invention are useful for gene therapy. As used herein, the phrase "gene therapy" refers to the transfer of genetic material (e.g., DNA or RNA) of interest into a host to treat or prevent a genetic or acquired disease or condition. The genetic material of interest encodes a product (e.g., a protein polypeptide, peptide or functional RNA) whose production in vivo is desired. For example, the genetic material of interest can encode a hormone, receptor, enzyme or (poly)peptide of therapeutic value. In a specific embodiment, the subject invention utilizes a class of lipid molecules for use in non-viral gene therapy which can complex with nucleic acids as described in Hughes et al., U.S. Pat. No. 6,169,078, incorporated herein by reference, in which a disulfide linker is provided between a polar head group and a lipophilic tail group of a lipid.

These therapeutic compounds of the present invention effectively complex with DNA and facilitate the transfer of DNA through a cell membrane into the intracellular space of a cell to be transformed with heterologous DNA. Furthermore, these lipid molecules facilitate the release of heterologous DNA in the cell cytoplasm thereby increasing gene transfection during gene therapy in a human or animal.

Cationic lipid-polyanionic macromolecule aggregates may be formed by a variety of methods known in the art. Representative methods are disclosed by Felgner et al., *Proc. Natl. Acad. Sci. USA* 86: 7413-7417 (1987); Eppstein et al., U.S. Pat. No. 4,897,355; Behr et al., *Proc. Natl. Acad. Sci. USA* 86:6982-6986 (1989); Bangham et al., *J. Mol. Biol.* 23:238-252 (1965); Olson et al., *Biochim. Biophys. Acta* 557:9 (1979); Szoka, et al., *Proc. Natl. Acad. Sci.* 75:4194 (1978); Mayhew et al., *Biochim. Biophys. Acta* 775:169 (1984); Kim et al., *Biochim. Biophys. Acta* 728:339 (1983); and Fukunaga et al., *Endocrinol.* 115:757 (1984), all incorporated herein by reference. In general, aggregates may be formed by preparing lipid particles consisting of either (1) a cationic lipid or (2) a cationic lipid mixed with a colipid, followed by adding a polyanionic macromolecule to the lipid particles at about room temperature (about 18 to 26° C.). In general, conditions are chosen that are not conducive to deprotection of protected groups. In one embodiment, the mixture is then allowed to form an aggregate over a period of about 10 minutes to about 20 hours, with about 15 to 60 minutes most conveniently used. Other time periods may be appropriate for specific lipid types. The complexes may be formed over a longer period, but additional enhancement of transfection efficiency will not usually be gained by a longer period of complexing.

The compounds and methods of the subject invention can be used to intracellularly deliver a desired molecule, such as, for example, a polynucleotide, to a target cell. The desired polynucleotide can be composed of DNA or RNA or analogs thereof. The desired polynucleotides delivered using the present invention can be composed of nucleotide sequences that provide different functions or activities, such as nucleotides that have a regulatory function, e.g., promoter sequences, or that encode a polypeptide. The desired polynucleotide can also provide nucleotide sequences that are antisense to other nucleotide sequences in the cell. For example, the desired polynucleotide when transcribed in the cell can provide a polynucleotide that has a sequence that is antisense to other nucleotide sequences in the cell. The antisense sequences can hybridize to the sense strand sequences in the cell. Polynucleotides that provide antisense sequences can be readily prepared by the ordinarily skilled artisan. The desired polynucleotide delivered into the cell can also comprise a nucleotide sequence that is capable of forming a triplex complex with double-stranded DNA in the cell.

The following examples illustrate the preparation of modified annexin proteins of the invention and in vitro and in vivo assays for anticoagulant activity of modified annexin proteins. It is to be understood that the invention is not limited to the exemplary work described or to the specific details set forth in the examples.

EXAMPLES

Example 1

Modified Annexin Preparation

Annexins can be purified from human tissues or produced by recombinant technology. For instance, annexin V can be purified from human placentas as described by Funakoshi et al. (1987). Examples of recombinant products are the expression of annexin II and annexin V in *Escherichia coli* (Kang, H.-M., *Trends Cardiovasc. Med.* 9:92-102 (1999); Thiagarajan and Benedict, 1997, 2000). A rapid and efficient purification method for recombinant annexin V, based on $Ca^{2+}$-enhanced binding to phosphatidylserine-containing liposomes and subsequent elution by EDTA, has been described by Berger, *FEBS Lett.* 329:25-28 (1993). This procedure can be improved by the use of phosphatidylserine coupled to a solid phase support.

Annexins can be coupled to polyethylene glycol (PEG) by any of several well-established procedures (reviewed by Hermanson, 1996) in a process referred to as pegylation. The present invention includes chemically-derivatized annexin molecules having mono- or poly-(e.g., 2-4) PEG moieties. Methods for preparing a pegylated annexin generally include the steps of (a) reacting the annexin with polyethylene glycol (such as a reactive ester or aldehyde derivative of PEG) under conditions whereby the annexin becomes attached to one or more PEG groups and (b) obtaining the reaction product or products. In general, the optimal reaction conditions for the reactions must be determined case by case based on known parameters and the desired result. Furthermore, the reaction may produce different products having a different number of PEG chains, and further purification may be needed to obtain the desired product.

Conjugation of PEG to annexin V can be performed using the EDC plus sulfo-NHS procedure. EDC (1-ethyl-3-(3-dimethylaminopropyl)-carbodiimide hydrochloride) is used to form active ester groups with carboxylate groups using sulfo-NHS(N-hydroxysulfosuccinamide). This increases the stability of the active intermediate, which reacts with an amine to give a stable amide linkage. The conjugation can be carried out as described in Hermanson, 1996.

Bioconjugate methods can be used to produce homopolymers or heteropolymers of annexin; methods are reviewed by Hermanson, 1996. Recombinant methods can also be used to produce fusion proteins, e.g., annexin expressed with the Fc portion of immunoglobulin or another protein. The heterotetramer of annexin II with P11 has also been produced in *E. coli* (Kang et al., 1999). All of these procedures increase the molecular weight of annexin and have the potential to increase the half-life of annexin in the circulation and prolong its anticoagulant effect.

A homodimer of annexin V can be produced using a DNA construct shown schematically in FIG. 1 (5'-3' sense strand) (SEQ ID NO:4) and coding for an amino acid sequence represented by SEQ ID NO:6. In this example, the annexin V gene is cloned into the expression vector pCMV FLAG 2 (available from Sigma-Aldrich) at EcoRI and Bgl II sites. The exact sequences prior to and after the annexin V sequence are unknown and denoted as "x". It is therefore necessary to sequence the construct prior to modification to assure proper codon alignment. The pCMV FLAG 2 vector comes with a strong promotor and initiation sequence (Kozak) and start site (ATG) built in. The start codon before each annexin V gene must therefore be removed, and a strong stop for tight expression should be added at the terminus of the second annexin V gene. The vector also comes with an 8-amino acid peptide sequence that can be used for protein purification (asp-tyr-lys-asp-asp-asp-asp-lys) (SEQ ID NO:9). A 14-amino acid spacer with glycine-serine swivel ends allows optimal rotation between tandem genes. Addition of restriction sites PvuII and ScaI allow removal of the linker if necessary. Addition of a protease site allows cleavage of tandem proteins following expression. PreScission ™ protease is available from Amersham Pharmacia Biotech and can be used to cleave tandem proteins.

Human Annexin V has the following amino acid sequence:

(SEQ ID NO:3)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD

The nucleotide sequence of human annexin V, inserted as indicated in the DNA construct illustrated in FIG. 1, is as follows:

(SEQ ID NO:1)
GCACAGGTTCTCAGAGGCACTGTGACTGACTTCCCTGGATTTGATGAGCG

GGCTGATGCAGAAACTCTTCGGAAGGCTATGAAAGGCTTGGGCACAGATG

AGGAGAGCATCCTGACTCTGTTGACATCCCGAAGTAATGCTCAGCGCCAG

GAAATCTCTGCAGCTTTTAAGACTCTGTTTGGCAGGGATCTTCTGGATGA

CCTGAAATCAGAACTAACTGGAAAATTTGAAAAATTAATTGTGGCTCTGA

TGAAACCCTCTCGGCTTTATGATGCTTATGAACTGAAACATGCCTTGAAG

GGAGCTGGAACAAATGAAAAGTACTGACAGAAATTATTGCTTCAAGGAC

ACCTGAAGAACTGAGAGCCATCAAACAAGTTTATGAAGAAGAATATGGCT

CAAGCCTGGAAGATGACGTGGTGGGGGACACTTCAGGGTACTACCAGCGG

ATGTTGGTGGTTCTCCTTCAGGCTAACAGAGACCCTGATGCTGGAATTGA

-continued
TGAAGCTCAAGTTGAACAAGATGCTCAGGCTTTATTTCAGGCTGGAGAAC

TTAAATGGGGGACAGATGAAGAAAAGTTTATCACCATCTTTGGAACACGA

AGTGTGTCTCATTTGAGAAAGGTGTTTGACAAGTACATGACTATATCAGG

ATTTCAAATTGAGGAAACCATTGACCGCGAGACTTCTGGCAATTTAGAGC

AACTACTCCTTGCTGTTGTGAAATCTATTCGAAGTATACCTGCCTACCTT

GCAGAGACCCTCTATTATGCTATGAAGGGAGCTGGGACAGATGATCATAC

CCTCATCAGAGTCATGGTTTCCAGGAGTGAGATTGATCTGTTTAACATCA

GGAAGGAGTTTAGGAAGAATTTTGCCACCTCTCTTTATTCCATGATTAAG

GGAGATACATCTGGGGACTATAAGAAAGCTCTTCTGCTGCTCTGTGGAGA

AGATGAC

Example 2

In Vitro and In Vivo Assays

In vitro assays determine the ability of modified annexin proteins to bind to activated platelets. Annexin V binds to platelets, and this binding is markedly increased in vitro by activation of the platelets with thrombin (Thiagarajan and Tait, 1990; Sun et al., 1993). Preferably, the modified annexin proteins of the present invention are prepared in such a way that perform the function of annexin in that they bind to platelets and prevent protein S from binding to platelets (Sun et al., 1993). The modified annexin proteins also perform the function of exhibiting the same anticoagulant activity in vitro that unmodified annexin proteins exhibit. A method for measuring the clotting time is the activated partial thromboplastin time (Fritsma, in *Hemostasis and thrombosis in the clinical laboratory* (Corriveau, D. M. and Fritsma, G. A., eds) J. P. Lipincott Co., Philadelphia (1989), pp. 92-124, incorporated herein by reference).

In vivo assays determine the antithrombotic activity of annexin proteins. Annexin V has been shown to decrease venous thrombosis induced by a laser or photochemically in rats (Römisch et al., 1991). The maximal anticoagulant effect was observed between 15 and 30 minutes after intravenous administration of annexin V, as determined functionally by thromboelastography. The modified annexin proteins of the present invention preferably show more prolonged activity in such a model than unmodified annexin. Annexin V was also found to decrease fibrin accretion in a rabbit model of jugular vein thrombosis (Van Ryn-McKenna et al., 1993). Air injection was used to remove the endothelium, and annexin V was shown to bind to the treated vein but not to the control contralateral vein. Decreased fibrin accumulation in the injured vein was not associated with systemic anticoagulation. Heparin did not inhibit fibrin accumulation in the injured vein. The modified annexin proteins of the present invention preferably perform the function of annexin in this model of venous thrombosis. A rabbit model of arterial thrombosis was used by Thiagarajan and Benedict, 1997. A partially occlusive thrombus was formed in the left carotid artery by application of an electric current. Annexin V infusion strongly inhibited thrombosis as manifested by measurements of blood flow, thrombus weight, labeled fibrin deposition and labeled platelet accumulation. Recently, a mouse model of photochemically-induced thrombus in cremaster muscles was introduced (Vollmar et al. *Thromb. Haemost.* 85:160-164 (2001), incorporated herein by reference). Using this technique, thrombosis can be induced in any desired artery or vein. The modified annexin proteins of the present invention preferably perform the function of annexin in such models, even when administered by bolus injection.

Example 3

The anticoagulant ability of human recombinant annexin V and pegylated human recombinant annexin V were compared in vitro.

Annexin V production. The polymerase chain reaction was used to amplify the cDNA from the initiator methionine to the stop codon with specific oligonucleotide primers from a human placental cDNA library. The forward primer was 5'-ACCTGAGTAGTCGCCATGGCACAGGTTCTC-3' (SEQ ID NO:7) and the reverse primer was 5'-CCCGAAT-TCACGTTAGTCATCTTCTCCACAGAGCAG-3' (SEQ ID NO:8). The amplified 1.1-kb fragment was digested with Nco I and Eco RI and ligated into the prokaryotic expression vector pTRC 99A. The ligation product was used to transform competent *Escherichia coli* strain JM 105 and sequenced.

Recombinant annexin V was isolated from the bacterial lysates as described by Berger et al., 1993, with some modification. An overnight culture of *E. coli* JM 105 transformed with pTRC 99A-annexin V was expanded 50-fold in fresh Luria-Bertrani medium containing 100 mg/L ampicillin. After 2 hours, isopropyl β-D-thiogalactopyranoside was added to a final concentration of 1 mmol/L. After 16 hours of induction, the bacteria were pelleted at 3500 g for 15 minutes at 4° C. The bacterial pellet was suspended in TBS, pH 7.5, containing 1 mmol/L PMSF, 5 mmol/L EDTA, and 6 mol/L urea. The bacterial suspension was sonicated with an ultrasonic probe at a setting of 6 on ice for 3 minutes. The lysate was centrifuged at 10,000 g for 15 minutes, and the supernatant was dialyzed twice against 50 vol TBS containing 1 mmol/L EDTA and once against 50 vol TBS.

Multilamellar liposomes were prepared by dissolving phosphatidylserine, lyophilized bovine brain extract, cholesterol, and dicetylphosphate in chloroform in a molar ration of 10:15:1 and dried in a stream of nitrogen in a conical flask. TBS (5 mL) was added to the flask and agitated vigorously in a vortex mixer for 1 minute. The liposomes were washed by centrifugation at 3500 g for 15 minutes, then incubated with the bacterial extract, and calcium chloride was added to a final concentration of 5 mmol/L. After 15 minutes of incubation at 37° C., the liposomes were sedimented by centrifugation at 10,000 g for 10 minutes, and the bound annexin V was eluted with 10 mmol/L EDTA. The eluted annexin V was concentrated by Amicon ultrafiltration and loaded onto a Sephacryl S 200 column. The annexin V was recovered in the included volume, whereas most of the liposomes were in the void volume. Fractions containing annexin V were pooled and dialyzed in 10 mmol/L Tris and 2 mmol/L EDTA, pH 8.1, loaded onto an anion exchange column, and eluted with a linear gradient of 0 to 200 mmol/L NaCl in the same buffer. The purified preparation showed a single band in SDS-PAGE under reducing conditions.

The annexin V produced as above was pegylated using the method of Hermanson, 1996, as described above.

Figure 2:
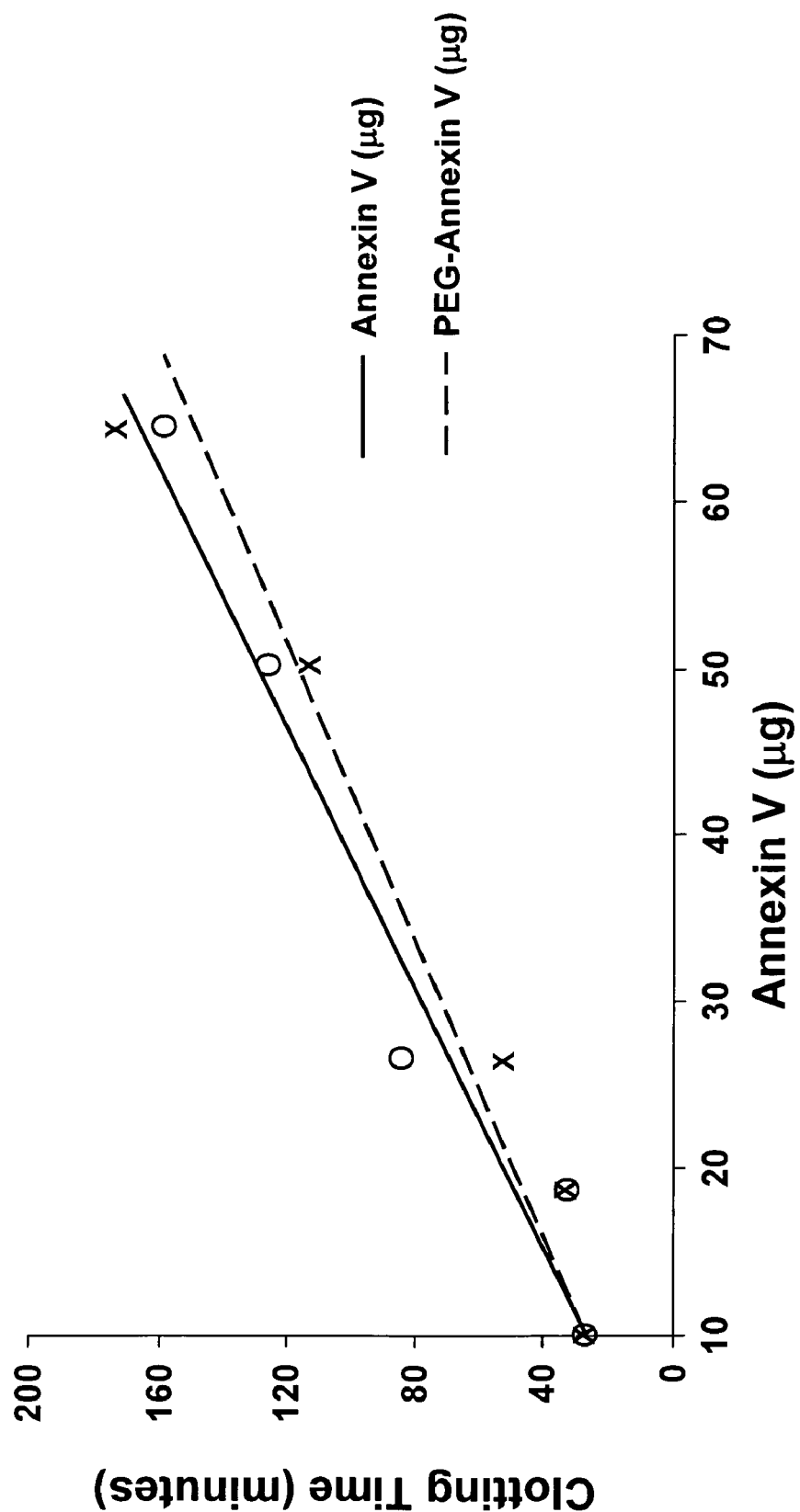
FIG. 2 is a plot of clotting time of an in vitro clotting assay comparing the anticoagulant potency of recombinant human annexin V and pegylated recombinant human annexin V.

Anti-coagulation assays. Prolongation of the clotting time (activated partial thromboplastin time) induced by annexin V and pegylated annexin V were compared. Activated partial thromboplastin times were assayed with citrated normal pooled plasma as described in Fritsma, 1989. Using different concentrations of annexin V and pegylated annexin V, produced as described above, dose-response curves for prolongation of clotting times were obtained. Results are shown in FIG. 2, a plot of clotting time versus annexin V and pegylated annexin V dose. As shown in the figure, the anticoagulant potency of the recombinant human annexin V and the pegylated recombinant human annexin V are substantially equivalent. The small difference observed is attributable to the change in molecular weight after pegylation. This experiment validates the assertion made herein that pegylation of annexin V can be achieved without significantly reducing its antithrombotic effects.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A pharmaceutical composition comprising a therapeutically effective amount of an isolated fusion protein and an excipient, said fusion protein consisting essentially of a first annexin V protein coupled to a second annexin V protein by a linker and wherein said first annexin V protein and said second annexin V protein independently comprise a polypeptide selected from the group consisting of:
   a) a polypeptide comprising the amino acid sequence of SEQ ID NO: 3; and
   b) a polypeptide comprising an amino acid sequence having at least 95% sequence identity to the amino acid sequence of SEQ ID NO:3, wherein the polypeptide exhibits phosphatidylserine binding activity.

2. A pharmaceutical composition comprising a therapeutically effective amount of an isolated fusion protein and an excipient, said fusion protein consisting essentially of a first annexin V protein coupled to a second annexin V protein by a linker and wherein said first annexin V protein and said second annexin V protein independently comprise a polypeptide selected from the group consisting of:
   a) a polypeptide comprising the amino acid sequence of SEQ ID NO: 3; and
   b) a polypeptide comprising an amino acid sequence having at least 95% sequence identity to the amino acid sequence of SEQ ID NO:3, wherein the polypeptide exhibits platelet binding activity.

3. A pharmaceutical composition comprising a therapeutically effective amount of an isolated fusion protein and an excipient, said fusion protein consisting essentially of a first annexin V protein coupled to a second annexin V protein by a linker and wherein said first annexin V protein and said second annexin V protein independently comprise a polypeptide selected from the group consisting of:
   a) a polypeptide comprising the amino acid sequence of SEQ ID NO: 3; and
   b) a polypeptide comprising an amino acid sequence having at least 95% sequence identity to the amino acid sequence of SEQ ID NO:3, wherein the polypeptide exhibits anticoagulation activity.

* * * * *